(12) United States Patent
Yeung

(10) Patent No.: US 6,699,980 B1
(45) Date of Patent: Mar. 2, 2004

(54) NUCLEIC ACID MOLECULE ENCODING A MISMATCH ENDONUCLEASE AND METHODS OF USE THEREOF

(75) Inventor: Anthony T. Yeung, Huntingdon Valley, PA (US)

(73) Assignee: Fox Chase Cancer Center, Philadelphia, PA (US)

( * ) Notice: Subject to any disclaimer, the term of this patent is extended or adjusted under 35 U.S.C. 154(b) by 0 days.

(21) Appl. No.: 09/514,768

(22) Filed: Feb. 28, 2000

(51) Int. Cl.[7] ........................ C07H 21/02; C12N 15/00; C12N 1/20
(52) U.S. Cl. ................ 536/23.1; 435/320.1; 435/252.3
(58) Field of Search .............................. 435/183, 320.1, 435/252.3; 424/94.1; 530/350; 536/23.1

(56) References Cited

U.S. PATENT DOCUMENTS

| | | | |
|---|---|---|---|
| 5,459,039 A | 10/1995 | Modrich | |
| 5,571,676 A | 11/1996 | Shuber | |
| 5,869,245 A | 2/1999 | Yeung | |

FOREIGN PATENT DOCUMENTS

| | | |
|---|---|---|
| WO | WO 93/20233 | 10/1993 |
| WO | WO 95/29251 | 11/1995 |

OTHER PUBLICATIONS

Harris et al (J. Am. Soc. Nephrology, 1995, 6:1125–33).*
Ahn et al (Nature genetics, 1993, 3(4)283–291).*
Cawthorn et al (Genomics, 1991, 9(3)446–460).*
Reiger et al (Glossary of Genetics and Cytogenetics, Classical and Molecular, 4th Ed., Springer–Verlag, Berlin, 1976, p. 17).*
Boehringer Mannheim Biochemicals, 1994 Catalog, p. 93.*
Aoyagi et al (FEBS Lett., 1998, 429(2)134–138).*
Bowie et al., Science, 1990, vol. 247, pp. 1306–1310.*
Burgess et al., J of Cell Bio. vol. 111, pp. 2129–2138, 1990.*
Lazar et al., Molecular and Cellular Biology, 1988, vol. 8, pp. 1247–1252.*

Bork, Genome Research, 2000, vol. 10, pp. 398–400.*
A–Lien Lu, 1992, Genomics 14, 249–255.
Miguel A. Perez–Amador, Jan. 2000, vol. 122 pp. 169–179.
Rima Youil, Genomics 32, 431–435 (1996), Article No. 0138.
Jerry B. Dodgson, Biochemistry, vol. 16, No. 11, 1977, pp. 2374–2379.
Shin–San Su, The Journal of Biological Chemistry, vol. 263, No. 14, Issue of May 15, pp. 6829–6835, 1988.
Robert S. Lahue, Mutation Research, 198 (1988) 37–43 Elsevier.
Vadim Demidov, Nucleic Acids Research, 1993, vol. 21, No. 9, 2103–2107.
G. Roman Reddy, Proc. Natl. Sci. USA, vol. 90, pp. 9867–9871, Nov. 1993 Genetics.
A–Lien Lu, Cell, vol. 54, 805–812, Sep. 9, 1988.
Richard M. Myers, Science, vol. 230, pp. 1242–1246.
Kenneth D. Vernick, Nucleic Acids Research, vol. 16 No. 14, 1988.
Ulrich Baumann, Eur. J. Biochem. 170, 267–272 (1987).
Ulrich Baumann, Eur. J. Biochem, 161, 409–413 (1986).
M. Laskowski, Sr., Methods in Enzymology, vol. 65, 263–76, 1980.
Shin–San Su, Proc. Natl. Acad. Sci. USA, vol. 83, pp. 5057–5061, Jul. 1986 Biochemistry.
Tadas Panavas, Plant Molecular Biology 40: 237–248 1999.
Shigemi Aoyagi, FEBS Letters (1998) 429, 134 138.
Kazuhiko Maekawa, Eur.J. Biochem: 200, 651–661 (1991).
Bing Yang, Biochemisty 2000, 39, 3533–3541 (2000).

* cited by examiner

Primary Examiner—Susan Ungar
(74) Attorney, Agent, or Firm—Dann Dorfman Herrell & Skillman, P.C.

(57) ABSTRACT

Nucleic acid molecules encoding a mismatch endonuclease and its method of use for the detection of mutations in targeted polynucleotide sequences are provided, which facilitate the localization and identification of mutations, mismatches and genetic polymorphisms.

12 Claims, 13 Drawing Sheets

(3 of 13 Drawing Sheet(s) Filed in Color)

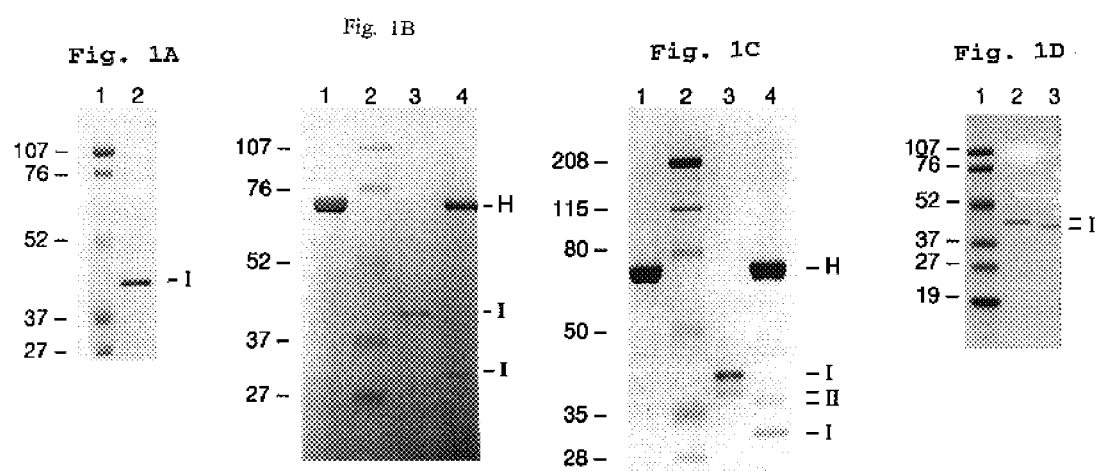

```
   1 GACAAGCGCCATCTATGAGTTTCATCATGCCTATATATAAACACATGAACCTGTCATTGT   60

61 TCATTTATGCATTATTGTTGTATTAGCTGAAAAATTTCTGGCAAATGACGCGATTATATT  120
                                                     M  T  R  L  Y  S  -

121 CTGTGTTCTTTCTTTTGTTGGCTCTTGTAGTTGAACCGGGTGTTAGAGCCTGGAGCAAAG  180
      V  F  F  L  L  A  L  V  V  E  P  G  V  R  A  W  S  K  E  -
                                                    ↑+

181 AAGGCCATGTCATGACATGTCAAATTGCGCAGGATCTGTTGGAGCCAGAAGCAGCACATG  240
      G  H  V  M  T  C  Q  I  A  Q  D  L  L  E  P  E  A  A  H  A  -
      +

241 CTGTAAAGATGCTGTTACCGGACTATGCTAATGGCAACTTATCGTCGCTGTGTGTGTGGC  300
      V  K  M  L  L  P  D  Y  A  N  G  N  L  S  S  L  C  V  W  P  -

301 CTGATCAAATTCGACACTGGTACAAGTACAGGTGGACTAGCTCTCTCCATTTCATCGATA  360
      D  Q  I  R  H  W  Y  K  Y  R  W  T  S  S  L  H  F  I  D  T  -
                               +                    +

361 CACCTGATCAAGCCTGTTCATTTGATTACCAGAGAGACTGTCATGATCCACATGGAGGGA  420
      P  D  Q  A  C  S  F  D  Y  Q  R  D  C  H  D  P  H  G  G  K  -
               #                    #

421 AGGACATGTGTGTTGCTGGAGCCATTCAAAATTTCACATCTCAGCTTGGACATTTCCGCC  480
      D  M  C  V  A  G  A  I  Q  N  F  T  S  Q  L  G  H  F  R  H  -
            #

481 ATGGAACATCTGATCGTCGATATAATATGACAGAGGCTTTGTTATTTTTATCCCACTTCA  540
      G  T  S  D  R  R  Y  N  M  T  E  A  L  L  F  L  S  H  F  M  -
                                                          +

541 TGGGAGATATTCATCAGCCTATGCATGTTGGATTTACAAGTGATATGGGAGGAAACAGTA  600
      G  D  I  H  Q  P  M  H  V  G  F  T  S  D  M  G  G  N  S  I  -
         +     +

601 TAGATTTGCGCTGGTTTCGCCACAAATCCAACCTGCACCATGTTTGGGATAGAGAGATTA  660
      D  L  R  W  F  R  H  K  S  N  L  H  H  V  W  D  R  E  I  I  -
                               +              +

661 TTCTTACAGCTGCAGCAGATTACCATGGTAAGGATATGCACTCTCTCCTACAAGACATAC  720
      L  T  A  A  A  D  Y  H  G  K  D  M  H  S  L  L  Q  D  I  Q  -

721 AGAGGAACTTTACAGAGGGTAGTTGGTTGCAAGATGTTGAATCCTGGAAGGAATGTGATG  780
      R  N  F  T  E  G  S  W  L  Q  D  V  E  S  W  K  E  C  D  D  -

781 ATATCTCTACTTGCGCCAATAAGTATGCTAAGGAGAGTATAAAACTAGCCTGTAACTGGG  840
      I  S  T  C  A  N  K  Y  A  K  E  S  I  K  L  A  C  N  W  G  -
                  #                                      #

841 GTTACAAAGATGTTGAATCTGGCGAAACTCTGTCAGATAAATACTTCAACACAAGAATGC  900
      Y  K  D  V  E  S  G  E  T  L  S  D  K  Y  F  N  T  R  M  P  -

901 CAATTGTCATGAAACGGATAGCTCAGGGTGGAATCCGTTTATCCATGATTTTGAACCGAG  960
      I  V  M  K  R  I  A  Q  G  G  I  R  L  S  M  I  L  N  R  V  -

961 TTCTTGGAAGCTCCGCAGATCATTCTTTGGCATGAATTTAGATACTGATATTCGCATTTC 1020
      L  G  S  S  A  D  H  S  L  *

1021 TCATGACACCCTTCTCTTATGCAATTTGCAGATCAGCTGTGATTCACTAATTGAA       1075
```

Figure 2

```
1 S1                                                                                                                               77
2 P1                                                                                                                               78
     WGNLGHETVAY-IAQ SFVASSTESFCQNIL GDDSTSYLA NVATWADTYKYTDAG EFSKPYHFIDAQDNP P-QSCGVDYDR
     WGALGHATVAY-VAQ HYVSPEAASWAQGIL GSSSSSYLA SIASWADEYRLTSAG KWSASLHFIDAEDNP P-TNCNVDYER
          | helix a |   | helix b   |←---loop 1 spacer----→|  loop 1 active site------→|
3 CELI  WSKEGHVMTCQ-IAQ DLLEPEAAHAVKMLL PDYANGNLS SLCVWPDQIRHWYKY RWTSSLHFIDTPDQA ----CSFDYQR  75
4 Zen1  WSKEGHVMTCQ-IAQ ELLSPDAAHAVQMLL PDYVKGNLS ALCVWPDQIRHWYRY RWTSPLHFIDTPDDA ----CSFDYTR  75
5 DSA6  WSKEGHIVTCR-IAQ DLLEPEAAETVRNLL PHYVDGDLS ALCTWPDQIRHWYKY RWSSPLHFIDTPDDA ----CSFDYSR  75
6 BFN1  WSKEGHILTCR-IAQ NLLEAGPAHVENLL  PDYVKGDLS ALCVWPDQIRHWYKY RWTSHLHYIDTPDQA ----CSYEYSR  75
     Zn3 Zn3                                                                Zn1

1 S1    DCG-SAG-----CSIS AIQNYTNILL------ ESPNGSE-ALNALKF VVHIIGDIHQPLHDE NL----EAGGN GIDVTYDG---  141
2 P1    DCG-SSG-----CSIS AIANYTQRVS------ DSSLSSENHAEALRF LVHFIGDMTQPLHDE AY----AVGGN KINVTFDG---  143
         |  helix c   |                            |helix d points →|   floor of active site  |left cover
3 CELI  DCHDPHGGKDMCVAG AIQNFTSQLGH-FRH GTSDRRYNMTEALLF LSHFMGDIHQPMHVG FTS--DMGGN SIDLRWFR---  150
4 Zen1  DCHDSNGMVDMCVAG AIKNFTSQLSH-YQH GTSDRRYNMTEALLF VSHFMGDIHQPMHVG FTT--DEGGN TIDLRWFR---  150
5 DSA6  DCHDPKGAEDMCVAG AVHNYTTQLMH-YRD GTSDRRYNLTESLLF LSHFMGDIHQPMHVG FTS--DEGGN TINLRWFR---  150
6 BFN1  DCHDQHGLKDMCVDG AIQNFTSQLQH-YGE GTSDRRYNMTEALLF LSHFMGDIHQPMHVG FTS--DEGGN TIDLRWYK---  150
                                                                Zn1 Zn3

1 S1    ---ETTNLHH--IW DTNMPEEAAGGYSLS VA---KTYADLLTER IKTGTYSSKKDS--- -----WTDGIDIK--- DPVS     201
2 P1    ---YHDNLHS--DW DTYMPQKLIGGHALS DA---ESWAKTLVQN IESGNYTAQAIG--- -----WIKGDNIS--- EPIT     203
      of active site|   helix e    |    helix f on back |                         loop on back
3 CELI  ----HKSNLHH--VW DREIILTAAADYHGK DM--HSLLQDIQRN FTEGSWLQDVES--- ------WKECD---- DIST     207
4 Zen1  ----HKSNLHH--VW DREIILTAASELYDK DM--ESIQKAIQAN FTHGLWSDDVNS--- ------WKDCD---- DISN     207
5 DSA6  ----HKSNLHH--VW DREIILTALADYYGK DL--DAFQQDIQNN FTTGIWSDDTSS--- ------WGECD---- DLFS     207
6 BFN1  ----HKSNLHH--VW DREIILTALKENYDK NL--DLLQEDLEKN ITNGLWHDDLSS--- ------WTECN---- DLIA     207
                                                                         Zn2

1 S1    TSMIWAADA NTYVCSTVLDDGLAY INSTDLSGEYYDKSQ P-----VFEELIAKA GYRLAAWLDLIASQP S-----------   266
2 P1    TATRWASDA NALVCTVVMPHGAAA LQTGDLYPTYYDSVI D-----TIELQIAKG GYRLANWINEIHGSE IAK---------   270
        helix g on side|                  |helix h, longest, under sugar on  |back, COOH under sugar
3 CELI  CANKYAKES IKLACNWGYKDVESG E---TLSDKYFNTRM P-----IVMKRIAQG GIRLSMILNRVLGSS ADHSLA*      278
4 Zen1  CVNKYAKES IALACKWGYEGVEAG E---TLSDDYFDSRM P-----IVMKRIAQG GIRLSMILNRVFGSS SSLEDALVPT-  278
5 DSA6  CPKKWASES ISLACKWGYKGVTPG E---TLSDEYFNSRM P-----IVMKRIAQG GVRLAMVLNRVFSDH KQHIPPPT---  276
6 BFN1  CPHKYASES IKLACKWGYKGVKSG E---TLSEEYFNTRL P-----IVMKRIVQG GVRLAMILNRDFSDD HAIAGVAAT--  277
        helix g on side|                  |helix h, longest, under sugar on  |back, COOH under sugar
```

Fig. 10

SEQUENCE LISTING

<160> NUMBER OF SEQ ID NOS: 11

<210> SEQ ID NO 1
<211> LENGTH: 1075
<212> TYPE: DNA
<213> ORGANISM: Celery

<400> SEQUENCE: 1

```
gacaagcgcc atctatgagt ttcatcatgc ctatatataa acacatgaac ctgtcattgt      60
tcatttatgc attattgttg tattagctga aaaatttctg gcaaatgacg cgattatatt     120
ctgtgttctt tcttttgttg gctcttgtag ttgaaccggg tgttagagcc tggagcaaag     180
aaggccatgt catgacatgt caaattgcgc aggatctgtt ggagccagaa gcagcacatg     240
ctgtaaagat gctgttaccg gactatgcta atggcaactt atcgtcgctg tgtgtgtggc     300
ctgatcaaat tcgacactgg tacaagtaca ggtggactag ctctctccat ttcatcgata     360
cacctgatca agcctgttca tttgattacc agagagactg tcatgatcca catggaggga     420
aggacatgtg tgttgctgga gccattcaaa atttcacatc tcagcttgga catttccgcc     480
atggaacatc tgatcgtcga tataatatga cagaggcttt gttattttta tcccacttca     540
tgggagatat tcatcagcct atgcatgttg gatttacaag tgatatggga ggaaacagta     600
tagatttgcg ctggtttcgc cacaaatcca acctgcacca tgtttgggat agagagatta     660
ttcttacagc tgcagcagat taccatggta aggatatgca ctctctccta caagacatac     720
agaggaactt tacagagggt agttggttgc aagatgttga atcctggaag gaatgtgatg     780
atatctctac ttgcgccaat aagtatgcta aggagagtat aaaactagcc tgtaactggg     840
gttacaaaga tgttgaatct ggcgaaactc tgtcagataa atacttcaac acaagaatgc     900
caattgtcat gaaacggata gctcagggtg gaatccgttt atccatgatt ttgaaccgag     960
ttcttggaag ctccgcagat cattctttgg catgaattta gatactgata ttcgcatttc    1020
tcatgacacc cttctcttat gcaatttgca gatcagctgt gattcactaa ttgaa         1075
```

<210> SEQ ID NO 2
<211> LENGTH: 296
<212> TYPE: PRT
<213> ORGANISM: Celery

<400> SEQUENCE: 2

```
Met Thr Arg Leu Tyr Ser Val Phe Phe Leu Leu Leu Ala Leu Val Val
  1               5                  10                  15

Glu Pro Gly Val Arg Ala Trp Ser Lys Glu Gly His Val Met Thr Cys
             20                  25                  30
```

```
Gln Ile Ala Gln Asp Leu Leu Glu Pro Glu Ala Ala His Ala Val Lys
         35                  40                  45

Met Leu Leu Pro Asp Tyr Ala Asn Gly Asn Leu Ser Ser Leu Cys Val
 50                  55                  60

Trp Pro Asp Gln Ile Arg His Trp Tyr Lys Tyr Arg Trp Thr Ser Ser
 65                  70                  75                  80

Leu His Phe Ile Asp Thr Pro Asp Gln Ala Cys Ser Phe Asp Tyr Gln
                 85                  90                  95

Arg Asp Cys His Asp Pro His Gly Gly Lys Asp Met Cys Val Ala Gly
             100                 105                 110

Ala Ile Gln Asn Phe Thr Ser Gln Leu Gly His Phe Arg His Gly Thr
         115                 120                 125

Ser Asp Arg Arg Tyr Asn Met Thr Glu Ala Leu Leu Phe Leu Ser His
 130                 135                 140

Phe Met Gly Asp Ile His Gln Pro Met His Val Gly Phe Thr Ser Asp
145                 150                 155                 160

Met Gly Gly Asn Ser Ile Asp Leu Arg Trp Phe Arg His Lys Ser Asn
                 165                 170                 175

Leu His His Val Trp Asp Arg Glu Ile Ile Leu Thr Ala Ala Ala Asp
             180                 185                 190

Tyr His Gly Lys Asp Met His Ser Leu Leu Gln Asp Ile Gln Arg Asn
         195                 200                 205

Phe Thr Glu Gly Ser Trp Leu Gln Asp Val Glu Ser Trp Lys Glu Cys
 210                 215                 220

Asp Asp Ile Ser Thr Cys Ala Asn Lys Tyr Ala Lys Glu Ser Ile Lys
225                 230                 235                 240

Leu Ala Cys Asn Trp Gly Tyr Lys Asp Val Glu Ser Gly Glu Thr Leu
                 245                 250                 255

Ser Asp Lys Tyr Phe Asn Thr Arg Met Pro Ile Val Met Lys Arg Ile
             260                 265                 270

Ala Gln Gly Gly Ile Arg Leu Ser Met Ile Leu Asn Arg Val Leu Gly
         275                 280                 285

Ser Ser Ala Asp His Ser Leu Ala
 290                 295

<210> SEQ ID NO 3
<211> LENGTH: 44
<212> TYPE: PRT
<213> ORGANISM: Celery
<220> FEATURE:
<221> NAME/KEY: misc_feature
<222> LOCATION: (36) and (41)
<223> OTHER INFORMATION: Xaa = any amino acid

<400> SEQUENCE: 3

Trp Ser Lys Glu Gly His Val Met Thr Cys Gln Ile Ala Gln Asp Leu
 1               5                  10                  15

Leu Glu Pro Glu Ala Ala His Ala Val Lys Met Leu Leu Pro Asp Tyr
                 20                  25                  30

Ala Asn Gly Xaa Leu Ser Ser Leu Xaa Val Trp Pro
             35                  40

<210> SEQ ID NO 4
<211> LENGTH: 8
<212> TYPE: PRT
<213> ORGANISM: Celery
<220> FEATURE:
<221> NAME/KEY: misc_feature
```

```
<222> LOCATION: (1)
<223> OTHER INFORMATION: Xaa = any amino acid

<400> SEQUENCE: 4

Xaa Ser Trp Leu Gln Asp Val Glu
  1               5

<210> SEQ ID NO 5
<211> LENGTH: 14
<212> TYPE: PRT
<213> ORGANISM: Celery

<400> SEQUENCE: 5

Cys Asp Asp Ile Ser Thr Cys Ala Asn Lys Tyr Ala Lys Glu
  1               5                  10

<210> SEQ ID NO 6
<211> LENGTH: 8
<212> TYPE: PRT
<213> ORGANISM: Celery

<400> SEQUENCE: 6

Leu Ala Cys Asn Trp Gly Tyr Lys
  1               5

<210> SEQ ID NO 7
<211> LENGTH: 267
<212> TYPE: PRT
<213> ORGANISM: Aspirgillis oryzae

<400> SEQUENCE: 7

Trp Gly Asn Leu Gly His Glu Thr Val Ala Tyr Ile Ala Gln Ser Phe
  1               5                  10                  15

Val Ala Ser Ser Thr Glu Ser Phe Cys Gln Asn Ile Leu Gly Asp Asp
                 20                  25                  30

Ser Thr Ser Tyr Leu Ala Asn Val Ala Thr Trp Ala Asp Thr Tyr Lys
             35                  40                  45

Tyr Thr Asp Ala Gly Glu Phe Ser Lys Pro Tyr His Phe Ile Asp Ala
     50                  55                  60

Gln Asp Asn Pro Pro Gln Ser Cys Gly Val Asp Tyr Asp Arg Asp Cys
 65                  70                  75                  80

Gly Ser Ala Gly Cys Ser Ile Ser Ala Ile Gln Asn Tyr Thr Asn Ile
                 85                  90                  95

Leu Leu Glu Ser Pro Asn Gly Ser Glu Ala Leu Asn Ala Leu Lys Phe
            100                 105                 110

Val Val His Ile Ile Gly Asp Ile His Gln Pro Leu His Asp Glu Asn
            115                 120                 125

Leu Glu Ala Gly Gly Asn Gly Ile Asp Val Thr Tyr Asp Gly Glu Thr
        130                 135                 140

Thr Asn Leu His His Ile Trp Asp Thr Asn Met Pro Glu Glu Ala Ala
145                 150                 155                 160

Gly Gly Tyr Ser Leu Ser Val Ala Lys Thr Tyr Ala Asp Leu Leu Thr
                165                 170                 175

Glu Arg Ile Lys Thr Gly Thr Tyr Ser Ser Lys Asp Ser Trp Thr
            180                 185                 190

Asp Gly Ile Asp Ile Lys Asp Pro Val Ser Thr Ser Met Ile Trp Ala
                195                 200                 205

Ala Asp Ala Asn Thr Tyr Val Cys Ser Thr Val Leu Asp Asp Gly Leu
        210                 215                 220
```

```
Ala Tyr Ile Asn Ser Thr Asp Leu Ser Gly Glu Tyr Tyr Asp Lys Ser
225                 230                 235                 240

Gln Pro Val Phe Glu Glu Leu Ile Ala Lys Ala Gly Tyr Arg Leu Ala
            245                 250                 255

Ala Trp Leu Asp Leu Ile Ala Ser Gln Pro Ser
        260                 265

<210> SEQ ID NO 8
<211> LENGTH: 270
<212> TYPE: PRT
<213> ORGANISM: Penicillium citrinum

<400> SEQUENCE: 8

Trp Gly Ala Leu Gly His Ala Thr Val Ala Tyr Val Ala Gln His Tyr
1               5                   10                  15

Val Ser Pro Glu Ala Ala Ser Trp Ala Gln Gly Ile Leu Gly Ser Ser
            20                  25                  30

Ser Ser Ser Tyr Leu Ala Ser Ile Ala Ser Trp Ala Asp Glu Tyr Arg
            35                  40                  45

Leu Thr Ser Ala Gly Lys Trp Ser Ala Ser Leu His Phe Ile Asp Ala
    50                  55                  60

Glu Asp Asn Pro Pro Thr Asn Cys Asn Val Asp Tyr Glu Arg Asp Cys
65                  70                  75                  80

Gly Ser Ser Gly Cys Ser Ile Ser Ala Ile Ala Asn Tyr Thr Gln Arg
                85                  90                  95

Val Ser Asp Ser Ser Leu Ser Ser Glu Asn His Ala Glu Ala Leu Arg
            100                 105                 110

Phe Leu Val His Phe Ile Gly Asp Met Thr Gln Pro Leu His Asp Glu
        115                 120                 125

Ala Tyr Ala Val Gly Gly Asn Lys Ile Asn Val Thr Phe Asp Gly Tyr
130                 135                 140

His Asp Asn Leu His Ser Asp Trp Asp Thr Tyr Met Pro Gln Lys Leu
145                 150                 155                 160

Ile Gly Gly His Ala Leu Ser Asp Ala Glu Ser Trp Ala Lys Thr Leu
                165                 170                 175

Val Gln Asn Ile Glu Ser Gly Asn Tyr Thr Ala Gln Ala Ile Gly Trp
            180                 185                 190

Ile Lys Gly Asp Asn Ile Ser Glu Pro Ile Thr Thr Ala Thr Arg Trp
        195                 200                 205

Ala Ser Asp Ala Asn Ala Leu Val Cys Thr Val Val Met Pro His Gly
210                 215                 220

Ala Ala Ala Leu Gln Thr Gly Asp Leu Tyr Pro Thr Tyr Tyr Asp Ser
225                 230                 235                 240

Val Ile Asp Thr Ile Glu Leu Gln Ile Ala Lys Gly Gly Tyr Arg Leu
            245                 250                 255

Ala Asn Trp Ile Asn Glu Ile His Gly Ser Glu Ile Ala Lys
        260                 265                 270

<210> SEQ ID NO 9
<211> LENGTH: 278
<212> TYPE: PRT
<213> ORGANISM: Zinnia elegans

<400> SEQUENCE: 9

Trp Ser Lys Glu Gly His Val Met Thr Cys Gln Ile Ala Gln Glu Leu
1               5                   10                  15
```

```
Leu Ser Pro Asp Ala Ala His Ala Val Gln Met Leu Leu Pro Asp Tyr
            20                  25                  30

Val Lys Gly Asn Leu Ser Ala Leu Cys Val Trp Pro Asp Gln Ile Arg
            35                  40                  45

His Trp Tyr Arg Tyr Arg Trp Thr Ser Pro Leu His Phe Ile Asp Thr
        50                  55                  60

Pro Asp Ala Cys Ser Phe Tyr Thr Arg Asp Cys His Asp Ser
 65                  70                  75                  80

Asn Gly Met Val Asp Met Cys Val Ala Gly Ala Ile Lys Asn Phe Thr
                    85                  90                  95

Ser Gln Leu Ser His Tyr Gln His Gly Thr Ser Asp Arg Arg Tyr Asn
                100                 105                 110

Met Thr Glu Ala Leu Leu Phe Val Ser His Phe Met Gly Asp Ile His
            115                 120                 125

Gln Pro Met His Val Gly Phe Thr Thr Asp Glu Gly Gly Asn Thr Ile
        130                 135                 140

Asp Leu Arg Trp Phe Arg His Lys Ser Asn Leu His His Val Trp Asp
145                 150                 155                 160

Arg Glu Ile Ile Leu Thr Ala Ala Ser Glu Leu Tyr Asp Lys Asp Met
                165                 170                 175

Glu Ser Leu Gln Lys Ala Ile Gln Ala Asn Phe Thr His Gly Leu Trp
            180                 185                 190

Ser Asp Asp Val Asn Ser Trp Lys Asp Cys Asp Asp Ile Ser Asn Cys
        195                 200                 205

Val Asn Lys Tyr Ala Lys Glu Ser Ile Ala Leu Ala Cys Lys Trp Gly
        210                 215                 220

Tyr Glu Gly Val Glu Ala Gly Glu Thr Leu Ser Asp Tyr Phe Asp
225                 230                 235                 240

Ser Arg Met Pro Ile Val Met Lys Arg Ile Ala Gln Gly Gly Val Arg
                245                 250                 255

Leu Ser Met Ile Leu Asn Arg Val Phe Gly Ser Ser Ser Leu Glu
            260                 265                 270

Asp Ala Leu Val Pro Thr
            275

<210> SEQ ID NO 10
<211> LENGTH: 276
<212> TYPE: PRT
<213> ORGANISM: Hermocallis cultivar

<400> SEQUENCE: 10

Trp Ser Lys Glu Gly His Ile Val Thr Cys Arg Ile Ala Gln Asp Leu
 1               5                  10                  15

Leu Glu Pro Glu Ala Ala Glu Thr Val Arg Asn Leu Leu Pro His Tyr
            20                  25                  30

Val Asp Gly Asp Leu Ser Ala Leu Cys Thr Trp Pro Asp Gln Ile Arg
            35                  40                  45

His Trp Tyr Lys Tyr Arg Trp Ser Ser Pro Leu His Phe Ile Asp Thr
        50                  55                  60

Pro Asp Ala Cys Ser Phe Asp Ser Arg Asp Cys His Asp Pro
 65                  70                  75                  80

Lys Gly Ala Glu Asp Met Cys Val Ala Gly Ala Val His Asn Tyr Thr
                    85                  90                  95

Thr Gln Leu Met His Tyr Arg Asp Gly Thr Ser Asp Arg Arg Tyr Asn
                100                 105                 110
```

```
Leu Thr Glu Ser Leu Leu Phe Leu Ser His Phe Met Gly Asp Ile His
            115                 120                 125

Gln Pro Met His Val Gly Phe Thr Ser Asp Glu Gly Gly Asn Thr Ile
        130                 135                 140

Asn Leu Arg Trp Phe Arg His Lys Ser Asn Leu His His Val Trp Asp
145                 150                 155                 160

Arg Glu Ile Ile Leu Thr Ala Leu Ala Asp Tyr Tyr Gly Lys Asp Leu
                165                 170                 175

Asp Ala Phe Gln Gln Asp Leu Gln Asn Asn Phe Thr Thr Gly Ile Trp
            180                 185                 190

Ser Asp Asp Thr Ser Ser Trp Gly Glu Cys Asp Asp Leu Phe Ser Cys
            195                 200                 205

Pro Lys Lys Trp Ala Ser Glu Ser Ile Ser Leu Ala Cys Lys Trp Gly
        210                 215                 220

Tyr Lys Gly Val Thr Pro Gly Glu Thr Leu Ser Asp Glu Tyr Phe Asn
225                 230                 235                 240

Ser Arg Met Pro Ile Val Met Lys Arg Ile Ala Gln Gly Gly Val Arg
                245                 250                 255

Leu Ala Met Val Leu Asn Arg Val Phe Ser Asp His Lys Gln His Ile
            260                 265                 270

Pro Pro Pro Thr
            275

<210> SEQ ID NO 11
<211> LENGTH: 277
<212> TYPE: PRT
<213> ORGANISM: Arabidopsis thaliana

<400> SEQUENCE: 11

Trp Ser Lys Glu Gly His Ile Leu Thr Cys Arg Ile Ala Gln Asn Leu
  1               5                  10                  15

Leu Glu Ala Gly Pro Ala His Val Val Glu Asn Leu Leu Pro Asp Tyr
                20                  25                  30

Val Lys Gly Asp Leu Ser Ala Leu Cys Val Trp Pro Asp Gln Ile Arg
            35                  40                  45

His Trp Tyr Lys Tyr Arg Trp Thr Ser His Leu His Tyr Ile Asp Thr
        50                  55                  60

Pro Asp Gln Ala Cys Ser Tyr Glu Tyr Ser Arg Asp Cys His Asp Gln
 65                 70                  75                  80

His Gly Leu Lys Asp Met Cys Val Asp Gly Ala Ile Gln Asn Phe Thr
                85                  90                  95

Ser Gln Leu Gln His Tyr Gly Glu Gly Thr Ser Asp Arg Arg Tyr Asn
            100                 105                 110

Met Thr Glu Ala Leu Leu Phe Leu Ser His Phe Met Gly Asp Ile His
        115                 120                 125

Gln Pro Met His Val Gly Phe Thr Ser Asp Glu Gly Gly Asn Thr Ile
        130                 135                 140

Asp Leu Arg Trp Tyr Lys His Lys Ser Asn Leu His His Val Trp Asp
145                 150                 155                 160

Arg Glu Ile Ile Leu Thr Ala Leu Lys Glu Asn Tyr Asp Lys Asn Leu
                165                 170                 175

Asp Leu Leu Gln Glu Asp Leu Gly Lys Asn Ile Thr Asn Gly Leu Trp
            180                 185                 190

His Asp Asp Leu Ser Ser Trp Thr Glu Cys Asn Asp Leu Ile Ala Cys
            195                 200                 205
```

-continued

```
Pro His Lys Tyr Ala Ser Glu Ser Ile Lys Leu Ala Cys Lys Trp Gly
    210                 215                 220

Tyr Lys Gly Val Lys Ser Gly Glu Thr Leu Ser Glu Glu Tyr Phe Asn
225                 230                 235                 240

Thr Arg Leu Pro Ile Val Met Lys Arg Ile Val Gln Gly Gly Val Arg
                245                 250                 255

Leu Ala Met Ile Leu Asn Arg Asp Phe Ser Asp Asp His Ala Ile Ala
                260                 265                 270

Gly Val Ala Ala Thr
            275
```

NUCLEIC ACID MOLECULE ENCODING A MISMATCH ENDONUCLEASE AND METHODS OF USE THEREOF

Pursuant to 35 U.S.C. §202(c) it is acknowledged that the U.S. Government has certain rights in the invention described herein, which was made in part with funds from the National Institutes of Health, Grant Number, NIH CA71426.

FIELD OF THE INVENTION

This invention relates to materials and methods for the detection of mutations in targeted nucleic acids. More specifically, the invention provides nucleic acid molecules encoding a mismatch specific nuclease and methods of use of the enzyme that facilitate the genetic screening of hereditary diseases and cancer. The method is also useful for the detection of genetic polymorphisms.

BACKGROUND OF THE INVENTION

Several publications are referenced in this application by numerals in parenthesis in order to more fully describe the state of the art to which this invention pertains. Full citations for these references are found at the end of the specification. The disclosure of each of these publications is incorporated by reference in the present specification.

The sequence of nucleotides within a gene can be mutationally altered or "mismatched" in any of several ways, the most frequent of which being base-pair substitutions, frameshift mutations and deletions or insertions. These mutations can be induced by environmental factors, such as radiation and mutagenic chemicals; errors are also occasionally committed by DNA polymerases during replication. Many human disease states arise because fidelity of DNA replication is not maintained. Cystic fibrosis, sickle cell anemia and some cancers are caused by single base changes in the DNA resulting in the synthesis of aberrant or non-functional proteins.

The high growth rate of plants and the abundance of DNA intercalators in plants suggests an enhanced propensity for mismatch and frameshift lesions. Plants and fungi are known to possess an abundance of single-stranded specific nucleases that attack both DNA and RNA (9-14). Some of these, like the Nuclease α of *Ustilago maydis,* are suggested to take part in gene conversion during DNA recombination (15,16). Of these nucleases, S1 nuclease from *Aspergillus oryzue* (17), and P1 nuclease from *Penicillium citrinum* (18), and Mung Bean Nuclease from the sprouts of *Vigna radiata* (19-22) are the best characterized. S1, P1 and the Mung Bean Nuclease are Zn proteins active mainly near pH 5.0 while Nuclease α is active at pH 8.0. The single strandedness property of DNA lesions appears to have been used by a plant enzyme, SP nuclease, for bulky adduct repair. The nuclease SP, purified from spinach, is a singlestranded DNase, an RNase, and able to incise DNA at $TC_{6-4}$ dimers and cisplatin lesions, all at neutral pH (23,24).

In *Escherichia coli,* lesions of base-substitution and unpaired DNA loops are repaired by a methylation-directed long patch repair system. The proteins in this multienzyme system include MutH, MutL and MutS (1, 2). This system is efficient; but the C/C lesion and DNA loops larger than 4 nucleotides are not repaired. The MutS and MutL proteins are conserved from bacteria to humans, and appear to be able to perform similar repair roles in higher organisms. For some of the lesions not well repaired by the MutS/MutL system, and for gene conversion where short-patch repair systems may be more desirable, other mismatch repair systems with novel capabilities are needed.

Currently, the most direct method for mutational analysis is DNA sequencing, however it is also the most labor intensive and expensive. It is usually not practical to sequence all potentially relevant regions of every experimental sample. Instead some type of preliminary screening method is commonly used to identify and target for sequencing only those samples that contain mutations. Single stranded conformational polymorphism (SSCP) is a widely used screening method based on mobility differences between single-stranded wild type and mutant sequences on native polyacrylamide gels. Other methods are based on mobility differences in wild type/mutant heteroduplexes (compared to control homoduplexes) on native gels (heteroduplex analysis) or denaturing gels (denaturing gradient gel electrophoresis). While sample preparation is relatively easy in these assays, very exacting conditions for electrophoresis are required to generate the often subtle mobility differences that form the basis for identifying the targets that contain mutations. Another critical parameter is the size of the target region being screened. In general, SSCP is used to screen target regions no longer than about 200–300 bases. The reliability of SSCP for detecting single-base mutations is somewhat uncertain but is probably in the 70–90% range for targets less than 200 bases. As the size of the target region increases, the detection rate declines, for example in one study from 87% for 183 bp targets to 57% for targets 307 bp in length (35). The ability to screen longer regions in a single step would enhance the utility of any mutation screening method.

Another type of screening technique currently in use is based on cleavage of unpaired bases in heteroduplexes formed between wild type probes hybridized to experimental targets containing point mutations. The cleavage products are also analyzed by gel electrophoresis, as subfragments generated by cleavage of the probe at a mismatch generally differ significantly in size from full length, uncleaved probe and are easily detected with a standard gel system. Mismatch cleavage has been effected either chemically (osmium tetroxide, hydroxylamine) or with a less toxic, enzymatic alternative, using RNase A. The RNase A cleavage assay has also been used, although much less frequently, to screen for mutations in endogenous mRNA targets or for detecting mutations in DNA targets amplified by PCR. A mutation detection rate of over 50% was reported for the original RNase screening method (36).

A newer method to detect mutations in DNA relies on DNA ligase which covalently joins two adjacent oligonucleotides which are hybridized on a complementary target nucleic acid. The mismatch must occur at the site of ligation. As with other methods that rely on oligonucleotides, salt concentration and temperature at hybridization are crucial. Another consideration is the amount of enzyme added relative to the DNA concentration.

The methods mentioned above cannot reliably detect a base change in a nucleic acid which is contaminated with more than 80% of a background nucleic acid, such as normal or wild type sequences. Contamination problems are significant in cancer detection wherein a malignant cell, in circulation for example, is present in extremely low amounts. The methods now in use lack adequate sensitivity to be practically applied in the clinical setting.

A method for the detection of gene mutations with mismatch repair enzymes has been described by Lu-Chang and Hsu. See WO 93/20233. The product of the MutY gene which recognizes mispaired A/G residues is employed in conjunction with another enzyme described in the reference as an "all type enzyme" which can nick at all base pair mismatches. The enzyme does not detect insertions and deletions. Also, the all type enzyme recognizes different mismatches with differing efficiencies and its activity can be adversely affected by flanking DNA sequences. This method therefore relies on a cocktail of mismatch repair enzymes and/or combinations of DNA glycosylases to detect the variety of mutations that can occur in a given DNA molecule.

SUMMARY OF THE INVENTION

The present invention provides materials and methods for the detection of mutations or mismatches in a targeted polynucleotide strand. Nucleic acid molecules encoding a mismatch endonuclease and methods of use thereof are disclosed. Detection is achieved using an endonuclease encoded by the nucleic acid molecules of the invention in combination with a gel assay system that facilitates the screening and identification of altered base pairing in a targeted nucleic acid strand. The availability of the nucleic acid having the sequence of SEQ ID NO:1 facilitates the preparation of large amounts of purified CEL I enzyme for use in such an assay.

In a preferred embodiment of the invention, an isolated nucleic acid molecule having the sequence of SEQ ID NO:1 encoding an endonuclease protein from celery about 43 kDa and 309 amino acids in length is provided. The endonuclease protein comprises a plurality of α helical domains and a flexible carboxy terminal region. The nucleic acid may be DNA or cDNA.

DNA molecules for isolating genomic clones of the invention are also provided. Such sequences facilitate the identification and cloning of a CEL I gene comprising introns and exons, the exons encoding the CEL 1 protein and specifically hybridizing with the nucleic acid of SEQ ID NO:1. Isolated RNA molecules transcribed from the nucleic acid of SEQ ID NO: 1 are also within the scope of the present invention.

In another aspect of the invention, a polynucleotide which comprises a) a sequence encoding a protein or polypeptide having SEQ ID NO: 2; b) a sequence encoding the complementary sequence of a); b) a sequence of nucleotides shown in FIG. 2; and c) a fragment of any of the sequences in a), or b) is disclosed.

In a preferred embodiment of the invention, an oligonucleotide between about 10 and about 200 nucleotides in length, which specifically hybridizes with SEQ ID NO:1 is provided.

In yet another aspect, an antibody immunologically specific for the isolated CEL I protein is provided. The antibody may be monoclonal or polyclonal.

Plasmids and vectors comprising SEQ ID NO: 1 are also within the scope of the present invention. In one embodiment, the vector may be a retroviral vector.

In a preferred embodiment of the invention, the plasmids or vectors described above may be introduced into host cells. Host cells suitable for this purpose include, without limitation, bacterial cells, plant cells, insect cells, procaryotic cells, fungal and mammalian cells.

Transgenic animals comprising SEQ ID NO: 1 are included in the present invention and have utility for assessing CEL I activities in a mammalian milieu.

Methods employing the nucleic acids of the invention are also provided. In one embodiment, a method for screening test compounds for CEL I modulating activity are provided. A host cell expressing a CEL I encoding nucleic acid is provided. The host cell is then contacted with a compound suspected of modulating CEL I activity and CEL I modulating activity is assessed by an alteration in the endonuclease activity of CEL I.

In a particularly preferred embodiment of the invention, a method for determining a mutation in a target sequence of single stranded polynucleotide with reference to a non-mutated sequence of a polynucleotide that is hybridizable with the polynucleotide including the target sequence is disclosed. The sequences are amplified, labeled with a detectable marker, hybridized to one another, exposed to a plant endonuclease encoded by a nucleic acid molecule having greater than >60% identity to a nucleic acid having the sequence of SEQ ID NO: 1, and analyzed for the presence of the mutation. In an alternative embodiment, the endonuclease is CEL I and is encoded by SEQ ID NO: 1. The availability of a nucleic acid having a sequence of SEQ ID NO: 1 facilitates the production of large quantities of the CEL I endonuclease for use in the method above. Exemplary endonucleases having greater than 60% sequence identity to CEL I are encoded by ZEN1 from Zinnia, BFN1 from Arabidopis and DSA6 from daylily.

Mismatch-specific nucleases corresponding to CEL I have been detected in more than 14 plant species. It is therefore anticipated that many additional plants contain nuclease genes that produce a protein with a high percentage of identity to SEQ ID NO:2. This use of these ortholog nuclease sequences to produce CEL I-like activity is contemplated with regard to the present invention. The encoded CEL I nuclease and its orthologs possess the following activities: i) detection of all mismatches between said hybridized sequences; ii) recognition of sequence differences in polynucleotide strands between about 100 bp and about 3 kb in length; and iii) recognition of said mutation in a target polynucleotide sequence without substantial adverse effect caused by flanking polynucleotide sequences.

DNA molecules and cDNA molecules may be assessed in the method described above. The method may be used to advantage in the screening assays for identifying alterations in DNA associated with genetic diseases and predisposition to cancer.

In yet another embodiment of the invention, an isozyme of CEL I having endonuclease activity is provided. The CEL I isozyme has a molecular weight of 39 kd and is isolated from celery.

In order to more clearly set forth the parameters of the present invention, the following definitions are used:

The term "endonuclease" refers to an enzyme that can cleave DNA internally.

The term "base pair mismatch" indicates a base pair combination that generally does not form in nucleic acids according to Watson and Crick base pairing rules. For example, when dealing with the bases commonly found in DNA, namely adenine, guanine, cytosine and thymidine, base pair mismatches are those base combinations other than the A-T and G-C pairs normally found in DNA. As described herein, a mismatch may be indicated, for example as C/C meaning that a cytosine residue is found opposite another cytosine, as opposed to the proper pairing partner, guanine.

The phrase "DNA insertion or deletion" refers to the presence or absence of "matched" bases between two strands of DNA such that complementarity is not maintained over the region of inserted or deleted bases.

The term "complementary" refers to two DNA strands that exhibit substantial normal base pairing characteristics. Complementary DNA may contain one or more mismatches, however.

The phrase "flanking nucleic acid sequences" refers to those contiguous nucleic acid sequences that are 5' and 3' to the endonuclease cleavage site.

The term "multiplex analysis" refers to the simultaneous assay of pooled DNA samples according to the above described methods.

C>T indicates the substitution of a thymidine residue for a cytosine residue giving rise to a mismatch. Inappropriate substitution of any base for another giving rise to a mismatch or a polymorphism may be indicated this way.

N, N, N', N'-tetramethyl-6-carboxyrhodamine (TAMRA) is a fluorescent dye used to label DNA molecular weight standards which are in turn utilized as an internal standard for DNA analyzed by automated DNA sequencing.

Primers may be labeled fluorescently with 6-carboxyfluorescein (6-FAM). Alternatively primers may be labeled with 4, 7, 2', 7'-Tetrachloro-6-carboxyfluorescein (TET). Other alternative DNA labeling methods are known in the art and are contemplated to be within the scope of the invention.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An isolated nucleic acid (either DNA or RNA) may further represent a molecule produced directly by biological or synthetic means and separated from other components present during its production.

"Natural allelic variants", "mutants" and "derivatives" of particular sequences of nucleic acids refer to nucleic acid sequences that are closely related to a particular sequence but which may possess, either naturally or by design, changes in sequence or structure. By closely related, it is meant that at least about 60%, but often, more than 85%, of the nucleotides of the sequence match over the defined length of the nucleic acid sequence referred to using a specific SEQ ID NO. Changes or differences in nucleotide sequence between closely related nucleic acid sequences may represent nucleotide changes in the sequence that arise during the course of normal replication or duplication in nature of the particular nucleic acid sequence. Other changes may be specifically designed and introduced into the sequence for specific purposes, such as to change an amino acid codon or sequence in a regulatory region of the nucleic acid. Such specific changes may be made in vitro using a variety of mutagenesis techniques or produced in a host organism placed under particular selection conditions that induce or select for the changes. Such sequence variants generated specifically may be referred to as "mutants" or "derivatives" of the original sequence.

The terms "percent similarity", "percent identity" and "percent homology" when referring to a particular sequence are used as set forth in the University of Wisconsin GCG software program and are further discussed below.

The present invention also includes active portions, fragments, derivatives and functional or non-functional mimetics of CEL I polypeptides or proteins of the invention. An "active portion" of CEL I polypeptide means a peptide that is less than the full length CEL I polypeptide, but which retains measurable biological activity.

A "fragment" or "portion" of the CEL I polypeptide means a stretch of amino acid residues of at least about five to seven contiguous amino acids, often at least about seven to nine contiguous amino acids, typically at least about nine to thirteen contiguous amino acids and, most preferably, at least about twenty to thirty or more contiguous amino acids. A "derivative" of the CEL I polypeptide or a fragment thereof means a polypeptide modified by varying the amino acid sequence of the protein, e.g. by manipulation of the nucleic acid encoding the protein or by altering the protein itself. Such derivatives of the natural amino acid sequence may involve insertion, addition, deletion or substitution of one or more amino acids, and may or may not alter the essential activity of the original CEL I polypeptide.

Different "variants" of the CEL I polypeptide exist in nature. These variants may be alleles characterized by differences in the nucleotide sequences of the gene coding for the protein, or may involve different RNA processing or post-translational modifications. The skilled person can produce variants having single or multiple amino acid substitutions, deletions, additions or replacements. These variants may include inter alia: (a) variants in which one or more amino acids residues are substituted with conservative or non-conservative amino acids, (b) variants in which one or more amino acids are added to the CEL I polypeptide, (c) variants in which one or more amino acids include a substituent group, and (d) variants in which the CEL I polypeptide is fused with another peptide or polypeptide such as a fusion partner, a protein tag or other chemical moiety, that may confer useful properties to the CEL I polypeptide, such as, for example, an epitope for an antibody, a polyhistidine sequence, a biotin moiety and the like. Other CEL I polypeptides of the invention include variants in which amino acid residues from one species are substituted for the corresponding residue in another species, either at the conserved or non-conserved positions. In another embodiment, amino acid residues at non-conserved positions are substituted with conservative or non-conservative residues. The techniques for obtaining these variants, including genetic (suppressions, deletions, mutations, etc.), chemical, and enzymatic techniques are known to the person having ordinary skill in the art.

To the extent such allelic variations, analogues, fragments, derivatives, mutants, and modifications, including alternative nucleic acid processing forms and alternative post-translational modification forms result in derivatives of the CEL I polypeptide that retain any of the biological properties of the CEL I polypeptide, they are included within the scope of this invention.

The term "orthologs" as used herein refers to nucleases encoded by nucleic acid sequences whose polypeptide product has greater than 60% identity to the CEL I encoding sequence and whose gene products have similar three dimensional structure and biochemical activities of CEL I. The use of nucleases encoded by such orthologs in the methods of the invention is contemplated herein. Exemplary orthologs include, without limitation, ZEN1, BFN1 and DSA6.

The term "functional" as used herein implies that the nucleic or amino acid sequence is functional for the recited assay or purpose.

The phrase "consisting essentially of" when referring to a particular nucleotide or amino acid means a sequence having the properties of a given SEQ ID No:. For example, when used in reference to an amino acid sequence, the phrase includes the sequence per se and molecular modifications that would not affect the basic and novel characteristics of the sequence.

A "replicon" is any genetic element, for example, a plasmid, cosmid, bacmid, phage or virus, that is capable of replication largely under its own control. A replicon may be either RNA or DNA and may be single or double stranded.

A "vector" is a replicon, such as a plasmid, cosmid, bacmid, phage or virus, to which another genetic sequence or element (either DNA or RNA) may be attached so as to bring about the replication of the attached sequence or element.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The term "oligonucleotide," as used herein refers to primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15–25 or more nucleotides, although it may contain fewer nucleotides. The probes herein are selected to be "substantially" complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield an primer extension product. The primer may vary in length depending on the particular conditions and requirement of the application. For example, in diagnostic applications, the oligonucleotide primer is typically 15–25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

The term "substantially pure" refers to a preparation comprising at least 50–60% by weight of a given material (e.g., nucleic acid, oligonucleotide, protein, etc.). More preferably, the preparation comprises at least 75% by weight, and most preferably 90–95% by weight of the given compound. Purity is measured by methods appropriate for the given compound (e.g. chromatographic methods, agarose or polyacrylamide gel electrophoresis, HPLC analysis, and the like).

"Mature protein" or "mature polypeptide" shall mean a polypeptide possessing the sequence of the polypeptide after any processing events that normally occur to the polypeptide during the course of its genesis, such as protoelytic processing from a polyprotein precursor. In designating the sequence or boundaries of a mature protein, the first amino acid of the mature protein sequence is designated as amino acid residue 1.

The term "tag," "tag sequence" or "protein tag" refers to a chemical moiety, either a nucleotide, oligonucleotide, polynucleotide or an amino acid, peptide or protein or other chemical, that when added to another sequence, provides additional utility or confers useful properties, particularly in the detection or isolation, to that sequence. Thus, for example, a homopolymer nucleic acid sequence or a nucleic acid sequence complementary to a capture oligonucleotide may be added to a primer or probe sequence to facilitate the subsequent isolation of an extension product or hybridized product. In the case of protein tags, histidine residues (e.g., 4 to 8 consecutive histidine residues) may be added to either the amino- or carboxy-terminus of a protein to facilitate protein isolation by chelating metal chromatography. Alternatively, amino acid sequences, peptides, proteins or fusion partners representing epitopes or binding determinants reactive with specific antibody molecules or other molecules (e.g., flag epitope, c-myc epitope, transmembrane epitope of the influenza A virus hemaglutinin protein, protein A, cellulose binding domain, calmodulin binding protein, maltose binding protein, chitin binding domain, glutathione S-transferase, and the like) may be added to proteins to facilitate protein isolation by procedures such as affinity or immunoaffinity chromatography. Chemical tag moieties include such molecules as biotin, which may be added to either nucleic acids or proteins and facilitates isolation or detection by interaction with avidin reagents, and the like. Numerous other tag moieties are known to, and can be envisioned by, the trained artisan, and are contemplated to be within the scope of this definition.

The terms "transform", "transfect", "transduce", shall refer to any method or means by which a nucleic acid is introduced into a cell or host organism and may be used interchangeably to convey the same meaning. Such methods include, but are not limited to, transfection, electroporation, microinjection, PEG-fusion and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. In other manners, the introduced nucleic acid may exist in the recipient cell or host organism only transiently.

A "clone" or "clonal cell population" is a population of cells derived from a single cell or common ancestor by mitosis.

A "cell line" is a clone of a primary cell or cell population that is capable of stable growth in vitro for many generations.

An "immune response" signifies any reaction produced by an antigen, such as a protein antigen, in a host having a functioning immune system. Immune responses may be either humoral in nature, that is, involve production of immunoglobulins or antibodies, or cellular in nature, involving various types of B and T lymphocytes, dendritic cells, macrophages, antigen presenting cells and the like, or both. Immune responses may also involve the production or elaboration of various effector molecules such as cytokines, lymphokines and the like. Immune responses may be measured both in in vitro and in various cellular or animal systems.

An "antibody" or "antibody molecule" is any immunoglobulin, including antibodies and fragments thereof, that binds to a specific antigen. The term includes polyclonal, monoclonal, chimeric, and bispecific antibodies. As used herein, antibody or antibody molecule contemplates both an intact immunoglobulin molecule and an immunologically active portion of an immunloglobulin molecule such as those portions known in the art as Fab, Fab', F(ab')2 and F(v).

BRIEF DESCRIPTION OF THE DRAWINGS

The instant patent or application file contains at least one drawing executed in color. Copies of this patent or patent application publication with color drawing(s) will be provided by the Office upon request and payment of the necessary fee.

FIGS. 1A–1D depict SDS polyacrylamide gel analysis of purified CEL I and CEL II. FIG. 1A: Lane 1, molecular weight standards shown in KDa on the side. Lane 2, 1 μg of homogeneous CEL I enzyme. Panels B and C examine the mobility changes in the CEL I and CEL II protein bands due to EndoH$_f$ treatment. Samples in panel B contain only CEL I. Samples in Panel C contain a mixture of CEL I and CEL II. Panel D shows the mobility change of homogeneous CEL I after sulfhydryl reduction. The gels were stained with Gelcode Blue. FIG. 1B: Lane 1, Endo H$_f$. Lane 2: molecular weight standards. Lane 3, homogeneous CEL I, about 30 ng. Lane 4, CEL I digested with Endo H$_f$. FIG. 1C: Lane 1, Endo H$_f$. Lane 2: molecular weight standards. Lane 3, Purified CEL I with a small amount of CEL II. Lane 4, CEL I and CEL II digested with Endo H$_f$. FIG. 1D: Purified CEL I was boiled for 2 min in SDS sample buffer in the presence (lane 2) or absence (lane 3) of 1% β-mercaptoethanol. Lane 1: molecular weight standards. H=Endo H$_f$, I=CEL I, II=CEL II.

FIG. 2 shows the cDNA (SEQ ID NO: 1) and amino acid sequence (SEQ ID NO: 2) of CEL I. The amino acid sequences of CEL I determined by Edman degradation are shown in bold. They consist of-the N-terminal sequence: WSKEGHVMTCQIAQDLLEPEAAHAVKM-LLPDYANGXLSSLXVWP (SEQ ID NO: 3); internal peptide from GluC digest: XSWLQDVE (SEQ ID NO: 4); internal peptides from tryptic digest: CDDISTCANKYAKE (SEQ ID NO: 5) and LACNWGYK (SEQ ID NO: 6). The residues identical with DSA6, BFN1 and ZEN1 are underlined. The conserved cys residues are shown with # underneath. The nine conserved residues shown to be ligands for the three Zn atoms in P1 nuclease are shown with + underneath.

FIG. 10 shows a Clustal W alignment of CEL I amino acid sequence with homologous *sequences. The Genbank accession numbers of the homologous sequences are indicated in brackets. 1: (P24021) nuclease S1 of *Aspergillus oryzae*, SEQ ID NO: 7; 2: (P24289) nuclease P1 of *Penicillium citrinum*, SEQ ID NO: 8; 3: CEL I cDNA amino acid sequence, SEQ ID NO: 2, residues 23–296; 4: (AB003131) ZEN 1 endonuclease from *Zinnia elegans*, SEQ ID NO: 9; 5: (AF082031) daylily senescence-associated protein 6 (DSA6) of *Hermocallis hybrid cultivar*, SEQ ID NO: 10; 6: (U90264) bifunctional nuclease BFN1 of *Arabidopsis thaliana*, SEQ ID NO: 11. Clustal W Multiple Sequence Alignment Kim C. Worley, Human Genome Center—Baylor College of Medicine. dot.imgen.bcm.tmc.edu:9331/cgi-bin/mutli-align/multi-align.p1). The secondary structure of P1 nuclease (Volbeda, A., Lahm, A., Sakiyama, F., and Suck, D., EMBO J. (1991) 10:1607–1618 and Romier, C., Dominguez, R., Lahm, A., Dahl, O., and Suck, D., (1998) *Proteins: Structure Function and Genetics* 32: 414–424) is indicated. The nine residues that bind the three Zn atoms are indicated in bold. The corresponding Zn atoms to these residues are indicated beneath the alignment.

DETAILED DESCRIPTION OF THE INVENTION

Figure 3:
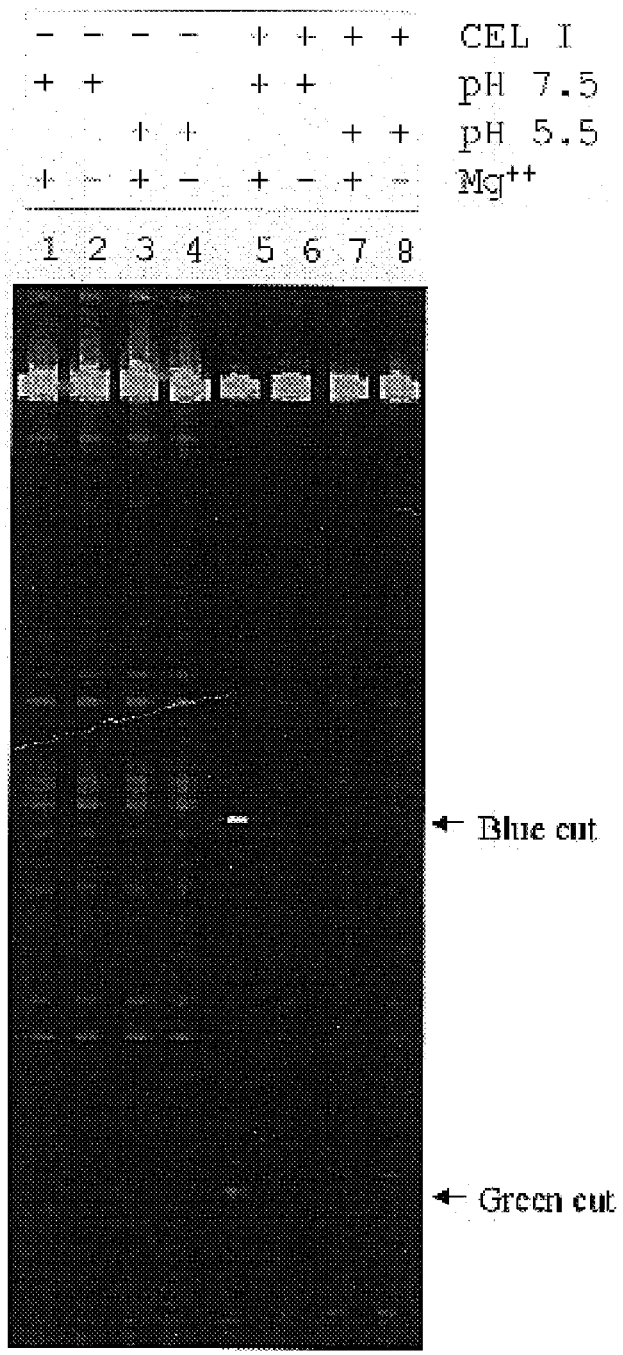
FIG. 3 is a picture of a gel image of mutation detection analyses on a Perkin Elmer automated DNA sequencer running the GeneScan program showing the effects of Mg++ and pH on CEL I mutation detection. The substrate is a 235 bp PCR product of the BRCA1 gene exon 5 containing a T→G polymorphism. It is labeled at the 5' terminus with 6-FAM (Blue) in the top strand and with TET (Green) on the bottom strand. The substrates were incubated with 0.5 units of CEL I for 30 min at 45 ° C. and then analyzed as described in FIG. 6. In lane 5 the band at 156 nt (labeled "blue cut") corresponds to CEL I mismatch-specific cutting on the 6-FAM-labeled strand, and the band at 80 nucleotides (labeled "green cut") corresponds to the mismatch-specific cutting on the TET-labeled strand. The bands at the bottom in the gel image show the internal size standards in each lane.
Figure 4A:
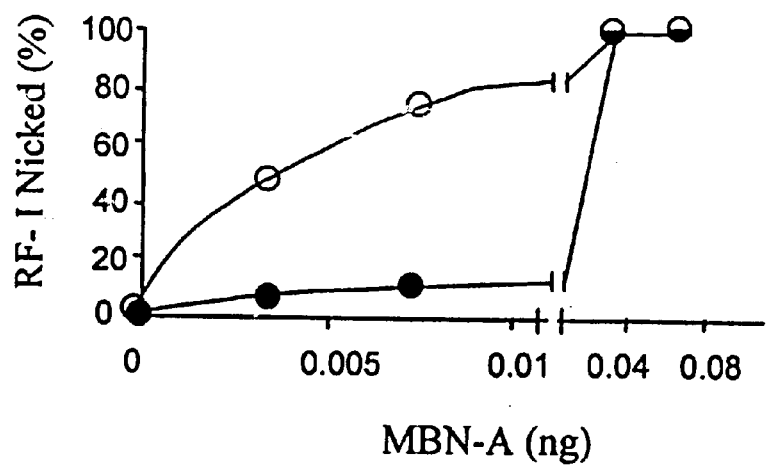
FIGS. 4A–4F show nicking of RF-I DNA by CEL I and mung bean nuclease. Assays are in the presence (solid symbols) or absence (hollow symbols) of 3 mM $MgCl_2$. Panels A, C, and E are assays at pH 5.5. Panels B, D, and F are at pH 7.5.
Figure 4B:
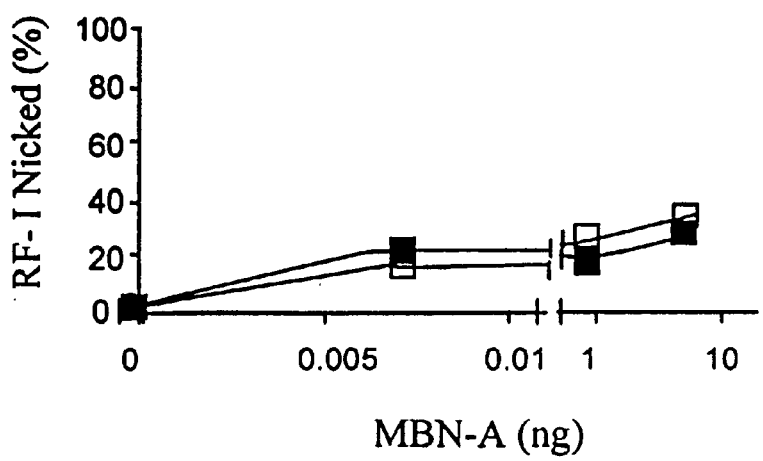
Figure 4C:
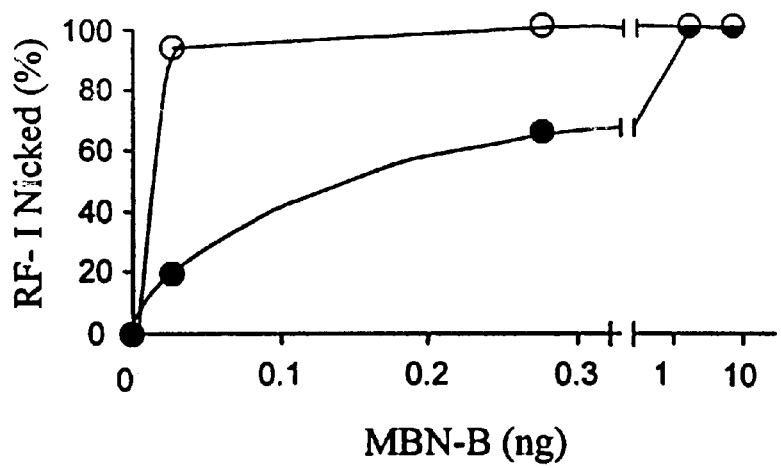
Figure 4D:
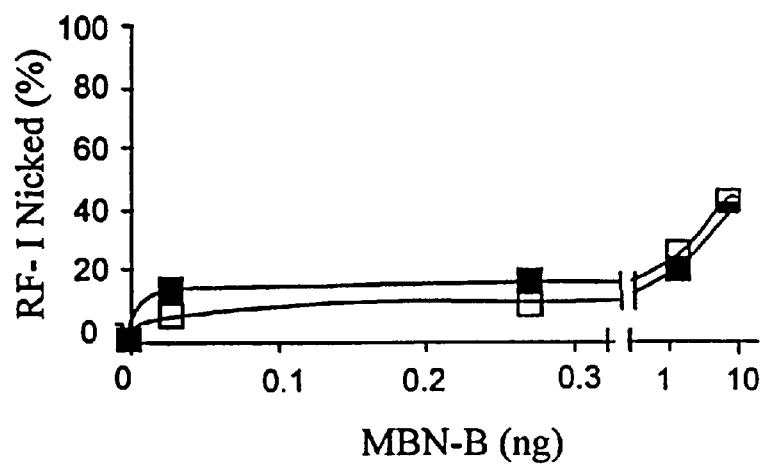
Figure 4E:
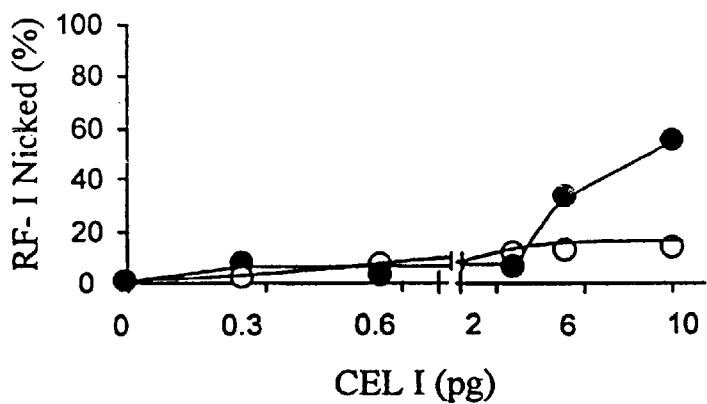
Figure 4F:
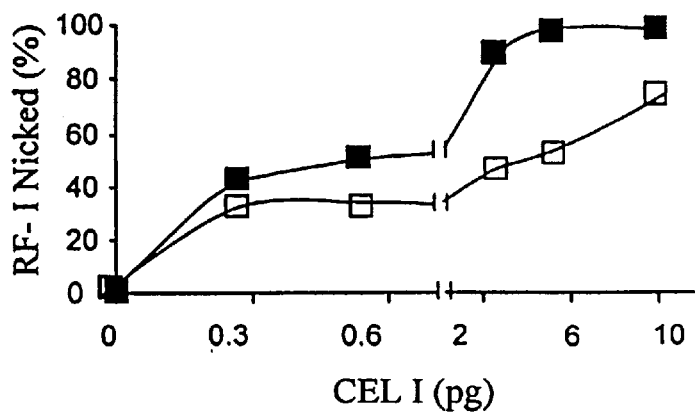

The enzymatic basis for the maintenance of correct base sequences during DNA replication has been extensively studied in *E. coli*. This organism has evolved a mismatch repair pathway that corrects a. variety of DNA basepair mismatches in hemimethylated DNA as well as insertions/deletions up to four nucleotides long. Cells deficient in this pathway mutate more frequently, hence the genes are called MutS, MutL and MutH etc. MutS protein binds to the mismatch and MutH is the endonuclease that incises the DNA at a GATC site on the strand in which the A residue is not methylated. MutL forms a complex with MutH and MutS during repair. Homologs of MutS and MutL, but not MutH exist in many systems. In yeast MSH2 (MutS homolog) can bind to a mismatch by itself, but a complex of two MutL homologs (MLH and PMS1) plus a MSH2 has been observed. The human homolog hMSH2 has evolved to bind to larger DNA insertions up to 14 nucleotides in length, which frequently arise by mechanisms such as misalignment at the microsatelite repeats in humans. Mutations in any one of these human homologs were shown to be responsible for the hereditary form of non-polyposis colon cancer (27, 28).

Celery contains over 40 µg of psoralen, a photoreactive intercalator, per gram of tissue (3). As a necessity, celery may possess a high capability for the repair of lesions of insertion, deletion, and other psoralen photoadducts. Single-strandedness at the site of the lesion is common to base substitution and DNA loop lesions. The data in the following examples demonstrate that celery possesses nucleic acid sequences which encode ample mismatch-specific endonuclease to deal with these potentially mutagenic events.

CEL I, isolated from celery, is the first eukaryotic nuclease known that cleaves DNA with high specificity at sites of base-substitution mismatch and DNA distortion. The enzyme requires Mg++ and Zn++ for activity, with pH optimum at neutral pH. We have purified CEL I 33,000 fold to apparent homogeneity. A key improvement is the use of α-methyl-mannoside in the purification buffers to overcome the aggregation of glycoproteins with endogenous lectins. The SDS gel electrophoresis band for the homogeneous CEL I, with and without the removal of its carbohydrate moieties, was extracted, renatured, and shown to have mismatch cutting specificity. After the determination of amino acid sequence of 28% of the CEL I polypeptide, we cloned the CEL I cDNA. Potential orthologs are nucleases putatively encoded by the genes BFN1 of Arabidopsis, ZEN1 of Zinnia, and DSA6 of daylily. Homology of CEL I with S1 and P1 nucleases are much lower. The nuclease activities of CEL I were characterized in comparison to the mung bean nuclease, the closest plant ortholog of S1 nuclease, to establish that these enzymes are catalytically distinct. Single-strandedness in a mismatch substrate does not appear to be the major feature recognized by CEL I. We propose that CEL I exemplifies a new family of neutral pH optimum, magnesium-stimulated, mismatch duplex-recognizing nucleases, within the S1 superfamily.

I. Preparation of CEL I-Encoding Nucleic Acid Molecules, CEL I Proteins, and Antibodies Thereto A. Nucleic Acid Molecules Nucleic acid molecules encoding the CEL I endonuclease of the invention may be prepared by two general methods: (1) Synthesis from appropriate nucleotide triphosphates; or (2) Isolation from biological sources. Both methods utilize protocols well known in the art.

The availability of nucleotide sequence information, such as the nearly full length cDNA having Sequence I.D. No. 1, enables preparation of an isolated nucleic acid molecule of the invention by oligonucleotide synthesis. Synthetic oligonucleotides may be prepared by the phosphoramidite method employed in the Applied Biosystems 380A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a 2.4 kb double-stranded molecule may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct an entire 2.4 kb double-stranded molecule. A synthetic DNA molecule so constructed may then be cloned and amplified in an appropriate vector. Nucleic acid sequences encoding CEL I may be isolated from appropriate biological sources using methods known in the art. In a preferred embodiment, a cDNA clone is isolated from a cDNA expression library of celery origin. In an alternative embodiment, utilizing the sequence information provided by the cDNA sequence, genomic clones encoding CEL I may be isolated. Alternatively, cDNA or genomic clones having homology with CEL I may be isolated from other plant species, using oligonucleotide probes corresponding to predetermined sequences within the CEL I gene.

In accordance with the present invention, nucleic acids having the appropriate level of sequence homology with the protein coding region of Sequence I.D. No. 1 may be identified by using hybridization and washing conditions of appropriate stringency. For example, hybridizations may be performed using a hybridization solution comprising: 5×SSC, 5×Denhardt's reagent, 0.5–1.0% SDS, 100 µg/ml denatured, fragmented salmon sperm DNA, 0.05% sodium pyrophosphate and up to 50% formamide. Hybridization is carried out at 37–42° C. for at least six hours. Following hybridization, filters are washed as follows: (1) 5 minutes at room temperature in 2×SSC and 0.5–1% SDS; (2) 15 minutes at room temperature in 2×SSC and 0.1% SDS; (3) 30 minutes-1 hour at 37° C. in 1×SSC and 1% SDS; (4) 2 hours at 42–65° in 1×SSC and 1% SDS, changing the solution every 30 minutes.

One common formula for calculating the stringency conditions required to achieve hybridization between nucleic acid molecules of a specified sequence homology is (Sambrook et al., 1989):

$$T_m = 81.5° C. + 16.6 \text{ Log } [Na+] + 0.41(\% \text{ G+C}) - 0.63(\% \text{ formamide}) - 600/\#bp \text{ in duplex}$$

As an illustration of the above formula, using [Na+]=[0.368] and 50% formamide, with GC content of 42% and an average probe size of 200 bases, the $T_m$ is 57° C. The $T_m$ of a DNA duplex decreases by 1–1.5° C. with every 1% decrease in homology. Thus, targets with greater than about 75% sequence identity would be observed using a hybridization temperature of 42° C. Such a sequence would be considered substantially homologous to the nucleic acid sequence of the present invention.

As can be seen from the above, the stringency of the hybridization and wash depend primarily on the salt concentration and temperature of the solutions. In general, to maximize the rate of annealing of the two nucleic acid molecules, the hybridization is usually carried out at salt and temperature conditions that are 20–25° C. below the calculated $T_m$ of the hybrid. Wash conditions should be as stringent as possible for the degree of identity of the probe for the target. In general, wash conditions are selected to be approximately 12–20° C. below the $T_m$ of the hybrid. In regards to the nucleic acids of the current invention, a moderate stringency hybridization is defined as hybridization in 6×SSC, 5×Denhardt's solution, 0.5% SDS and 100 µg/ml denatured salmon sperm DNA at 42° C., and wash in 2×SSC and 0.5% SDS at 55° C. for 15 minutes. A high stringency hybridization is defined as hybridization in 6×SSC, 5×Denhardt's solution, 0.5% SDS and 100 µg/ml denatured salmon sperm DNA at 42° C., and wash in 1×SSC and 0.5% SDS at 65° C. for 15 minutes. A very high stringency hybridization is defined as hybridization in 6×SSC, 5×Denhardt's solution, 0.5% SDS and 100 µg/ml denatured salmon sperm DNA at 42° C., and wash in 0.1×SSC and 0.5% SDS at 65° C. for 15 minutes.

Nucleic acids of the present invention may be maintained as DNA in any convenient cloning vector. In a preferred embodiment, clones are maintained in a plasmid cloning/expression vector, such as PBLUESCRIPT® (Stratagene, La Jolla, Calif.), which is propagated in a suitable *E. coli* host cell. Genomic clones of the invention encoding the CEL L gene may be maintained in lambda phage FIX® II (Stratagene).

CEL I-encoding nucleic acid molecules of the invention include cDNA, genomic DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule of the present invention, such as selected segments of the cDNA having Sequence I.D. No. 1. Such oligonucleotides are useful as probes for detecting or isolating CEL I genes.

It will be appreciated by persons skilled in the art that variants (e.g., allelic variants) of these sequences exist in the celery population, and must be taken into account when designing and/or utilizing oligos of the invention. Accordingly, it is within the scope of the present invention to encompass such variants, with respect to the CEL I sequences disclosed herein or the oligos targeted to specific locations on the respective genes or RNA transcripts. With respect to the inclusion of such variants, the term "natural allelic variants" is used herein to refer to various specific nucleotide sequences and variants thereof that would occur in a given DNA population. Genetic polymorphisms giving rise to conservative or neutral amino acid substitutions in the encoded protein are examples of such variants. Additionally, the term "substantially complementary" refers to oligo sequences that may not be perfectly matched to a target sequence, but the mismatches do not materially affect the ability of the oligo to hybridize with its target sequence under the conditions described.

Thus, the coding sequence may be that shown in Sequence I.D. No. 1, or it may be a mutant, variant, derivative or allele of this sequence. The sequence may differ from that shown by a change which is one or more of addition, insertion, deletion and substitution of one or more nucleotides of the sequence shown. Changes to a nucleotide sequence may result in an amino acid change at the protein level, or not, as determined by the genetic code.

Thus, nucleic acid according to the present invention may include a sequence different from the sequence shown in Sequence I.D. No. 1 yet encode a polypeptide with the same amino acid sequence.

On the other hand, the encoded polypeptide may comprise an amino acid sequence which differs by one or more amino acid residues from the amino acid sequence shown in Sequence I.D. No. 2. Nucleic acid encoding a polypeptide which is an amino acid sequence mutant, variant, derivative or allele of the sequence shown in Sequence I.D. No. 2 is further provided by the present invention. Nucleic acid encoding such a polypeptide may show greater than 60% identity with the coding sequence shown in Sequence I.D. No. 1, greater than about 70% identity, greater than about 80% identity, greater than about 90% identity or greater than about 95% identity.

The present invention provides a method of obtaining nucleic acid of interest, the method including hybridization of a probe having part or all of the sequence shown in Sequence I.D. No. 1 or a complementary sequence, to target nucleic acid. Hybridization is generally followed by identification of successful hybridization and isolation of nucleic acid which has hybridized to the probe, which may involve one or more steps of PCR.

Such oligonucleotide probes or primers, as well as the full-length sequence (and mutants, alleles, variants, and derivatives) are useful in screening a test sample containing nucleic acid for the presence of alleles, mutants or variants of CEL I, the probes hybridizing with a target sequence from a sample obtained from a plant being tested. The conditions of the hybridization can be controlled to minimize non-specific binding, and preferably stringent to moderately stringent hybridization conditions are used. The skilled person is readily able to design such probes, label them and devise suitable conditions for hybridization reactions, assisted by textbooks such as Sambrook et al (1989) and Ausubel et al (1992).

In some preferred embodiments, oligonucleotides according to the present invention that are fragments of the sequences shown in Sequence I.D. No. 1 or any allele associated with endonuclease activity, are at least about 10 nucleotides in length, more preferably at least 15 nucleotides in length, more preferably at least about 20 nucleotides in length. Such fragments themselves individually represent aspects of the present invention. Fragments and other oligonucleotides may be used as primers or probes as discussed but may also be generated (e.g. by PCR) in methods concerned with determining the presence in a test sample of a sequence encoding a homolog of CEL I nuclease.

B. Proteins

CEL I is the first eucaryotic nuclease identified which cleaves DNA with high specificity at sites of base-substitution mismatch and DNA distortion. A full-length CEL I protein of the present invention may be prepared in a variety of ways, according to known methods. The protein may be purified from appropriate sources, e.g., from celery as described in U.S. Pat. No. 5,869,245, the entire disclosure of which is incorporated by reference herein. However, this is not a preferred method due to the low amount of protein likely to be present in a given cell type at any time. The availability of nucleic acid molecules encoding CEL I enables production of the protein using in vitro expression methods known in the art. For example, a cDNA or gene may be cloned into an appropriate in vitro transcription vector, such as pSP64 or pSP65 for in vitro transcription,- followed by cell-free translation in a suitable cell-free translation system, such as wheat germ or rabbit reticulocyte lysates. In vitro transcription and translation systems are commercially available, e.g., from Promega Biotech, Madison, Wis. or BRL, Rockville, M.D.

Alternatively, according to a preferred embodiment, larger quantities of CEL I may be produced by expression in a suitable prokaryotic or eukaryotic system. For example, part or all of a DNA molecule, such as the cDNA having Sequence I.D. No. 1, may be inserted into a plasmid vector adapted for expression in a bacterial cell, such as *E. coli*. Such vectors comprise the regulatory elements necessary for expression of the DNA in the host cell (e.g. *E. coli*) positioned in such a manner as to permit expression of the DNA in the host cell. Such regulatory elements required for expression include promoter sequences, transcription initiation sequences and, optionally, enhancer sequences.

The CEL I produced by gene expression in a recombinant prokaryotic or eukaryotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6–8 histidine residues at their N-terminus or C-terminus. Alternative tags may comprise the FLAG epitope or the hemagglutinin epitope. Such methods are commonly used by skilled practitioners.

The CEL I proteins of the invention, prepared by the aforementioned methods, may be analyzed according to standard procedures. For example, such proteins may be subjected to amino acid sequence analysis, according to known methods.

Polypeptides which are amino acid sequence variants, alleles, derivatives or mutants are also provided by the present invention. A polypeptide which is a variant, allele, derivative, or mutant may have an amino acid sequence that differs from that given in Sequence I.D. No. 2 by one or more of addition, substitution, deletion and insertion of one or more amino acids. Preferred such polypeptides have CEL I function, that is to say have one or more of the following properties: ability to cleave mismatched heteroduplex DNA; immunological cross-reactivity with an antibody reactive with the polypeptide for which the sequence is given in Sequence I.D. No. 2; sharing an epitope with the polypeptide for which the sequence is given in Sequence I.D. No. 2 (as determined for example by immunological cross-reactivity between the two polypeptides.

A polypeptide which is an amino acid sequence variant, allele, derivative or mutant of the amino acid sequence shown in Sequence I.D. No. 2 may comprise an amino acid sequence which shares greater than about 35% sequence identity with the sequence shown, greater than about 40%, greater than about 50%, greater than about 60%, greater than about 70%, greater than about 80%, greater than about 90% or greater than about 95%. Particular amino acid sequence variants may differ from that shown in Sequence I.D. No.2 by insertion, addition, substitution or deletion of 1 amino acid, 2, 3, 4, 5–10, 10–20, 20–30, 30–40, 40–50, 50–100, 100–150, or more than 150 amino acids. For amino acid "homology", this may be understood to be identity or similarity (according to the established principles of amino acid similarity, e.g., as determined using the algorithm GAP (Genetics Computer Group, Madison, Wis.). GAP uses the Needleman and Wunsch algorithm to align two complete sequences that maximizes the number of matches and minimizes the number of gaps. Generally, the default parameters are used, with a gap creation penalty=12 and gap extension penalty =4. Use of GAP may be preferred but other algorithms may be used including without limitation, BLAST (Altschul et al. (1990 J. Mol. Biol. 215:405–410); FASTA (Pearson and Lipman (1998) PNAS USA 85:2444–2448) or the Smith Waterman alogrithm (Smith and Waterman (1981) J. Mol. Biol. 147:195–197) generally employing default parameters. Use of either of the terms "homology" and "homologous" herein does not imply any necessary evolutionary relationship between the compared sequences. The terms are used as they are in the phrase "homologous recombination", i.e., the terms merely require that the two nucleotide sequences are sufficiently similar to recombine under appropriate conditions.

A polypeptide according to the present invention may be used in screening for molecules which affect or modulate its activity or function. Such molecules may be useful for research purposes.

The present invention also provides antibodies capable of immunospecifically binding to proteins of the invention. Polyclonal antibodies directed toward CEL I may be prepared according to standard methods. In a preferred embodiment, monoclonal antibodies are prepared, which react immunospecifically with various epitopes of CEL I. Monoclonal antibodies may be prepared according to general methods of Kohler and Milstein, following standard protocols. Polyclonal or monoclonal antibodies that immunospecifically interact with CEL I can be utilized for identifying and purifying such proteins. For example, antibodies may be utilized for affinity separation of proteins with which they immunospecifically interact. Antibodies may also be used to immunoprecipitate proteins from a sample containing a mixture of proteins and other biological molecules. Other uses of anti-CEL I antibodies are described below.

Antibodies according to the present invention may be modified in a number of ways. Indeed the term "antibody" should be construed as covering any binding substance having a binding domain with the required specificity. Thus, the invention covers antibody fragments, derivatives, functional equivalents and homologues of antibodies, including synthetic molecules and molecules whose shape mimics that of an antibody enabling it to bind an antigen or epitope.

Exemplary antibody fragments, capable of binding an antigen or other binding partner, are Fab fragment consisting of the VL, VH, Cl and CH1 domains; the Fd fragment consisting of the VH and CH1 domains; the Fv fragment consisting of the VL and VH domains of a single arm of an antibody; the dAb fragment which consists of a VH domain; isolated CDR regions and F(ab')2 fragments, a bivalent fragment including two Fab fragments linked by a disulphide bridge at the hinge region. Single chain Fv fragments are also included.

II. Uses of CEL I-Encoding Nucleic Acids, CEL I Proteins and Antibodies Thereto

CEL I appears to be an DNA endonuclease which may be used to advantage in mutational screening assays. Specifically, the CEL I molecules of the invention may be used to advantage in genetic screening assays to identify those patients that may be at risk for certain genetic disorders. Such disorders include, without limitation, sickle cell anemia, cystic fibrosis, lysosomal storage diseases and genetic mutations that predispose a patient to cancer.

Additionally, CEL I nucleic acids, proteins and antibodies thereto, according to this invention, may be used as a research tool to identify other proteins that are intimately involved in DNA recognition and repair reactions. Biochemical elucidation of the DNA recognition and repair capacity of CEL I will facilitate the development of these novel screening assays for assessing a patient's propensity for cancer and genetic disease.

A. CEL I-Encoding Nucleic Acids

CEL I-encoding nucleic acids may be used for a variety of purposes in accordance with the present invention. CEL I-encoding DNA, RNA, or fragments thereof may be used as probes to detect the presence of and/or expression of genes encoding CEL I-like proteins. Methods in which CEL I-encoding nucleic acids may be utilized as probes for such assays include, but are not limited to: (1) in situ hybridization; (2) Southern hybridization (3) northern hybridization; and (4) assorted amplification reactions such as polymerase chain reactions (PCR).

The CEL I-encoding nucleic acids of the invention may also be utilized as probes to identify related genes from other plant and animal species. As is well known in the art, hybridization stringencies may be adjusted to allow hybridization of nucleic acid probes with complementary sequences of varying degrees of homology. Thus, CEL I-encoding nucleic acids may be used to advantage to identify and characterize other genes of varying degrees of relation to CEL I, thereby enabling further characterization of the DNA mismatch recognition system. Additionally, they may be used to identify genes encoding proteins that interact with CEL I (e.g., by the "interaction trap" technique), which should further accelerate identification of the components involved in DNA mismatch recognition.

Nucleic acid molecules, or fragments thereof, encoding CEL I may also be utilized to control the production of CEL I, thereby regulating the amount of protein available to participate in DNA mismatch recognition reactions. Alterations in the physiological amount of CEL I protein may dramatically affect the activity of other protein factors involved in DNA mismatch recognition.

The availability of CEL I encoding nucleic acids enables the production of strains of laboratory mice carrying part or all of the CEL I gene or mutated sequences thereof. Such mice may provide an in vivo model for assessing CEL I activity in a mammalian milieu. Methods of introducing transgenes in laboratory mice are known to those of skill in the art. Three common methods include: 1. integration of retroviral vectors encoding the foreign gene of interest into an early embryo; 2. injection of DNA into the pronucleus of a newly fertilized egg; and 3. the incorporation of genetically manipulated embryonic stem cells into an early embryo. Production of the transgenic mice described above will faciliate the molecular elucidation of the role CEL I plays in DNA mismatch recognition.

The term "animal" is used herein to include all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at the subcellular level, such as by targeted recombination or microinjection or infection with recombinant virus. The term "transgenic animal" is not meant to encompass classical cross-breeding or in vitro fertilization, but rather is meant to encompass animals in which one or more cells are altered by or receive a recombinant DNA molecule. This molecule may be specifically targeted to a defined genetic locus, be randomly integrated within a chromosome, or it may be extrachromosomally replicating DNA. The term "germ cell line transgenic animal" refers to a transgenic animal in which the genetic alteration or genetic information was introduced into a germ line cell, thereby conferring the ability to transfer the genetic information to offspring. If such offspring, in fact, possess some or all of that alteration or genetic information, then they, too, are transgenic animals.

B. CEL I Protein and Antibodies

Purified CEL I protein, or fragments thereof, produced via expression of the CEL I encoding nucleic acids of the present invention may be used to produce polyclonal or monoclonal antibodies which also may serve as sensitive detection reagents for the presence and accumulation of CEL I (or complexes containing CEL I) in plant cells. Recombinant techniques enable expression of fusion proteins containing part or all of the CEL I protein. The full length protein or fragments of the protein may be used to advantage to generate an array of monoclonal antibodies specific for various epitopes of the protein, thereby providing even greater sensitivity for detection of the protein in cells.

Polyclonal or monoclonal antibodies immunologically specific for CEL I may be used in a variety of assays designed to detect and quantitate the protein. Such assays include, but are not limited to: (1) flow cytometric analysis; (2) immunochemical localization of CEL I in plant cells; and (3) immunoblot analysis (e.g., dot blot, Western blot) of extracts from various cells. Additionally, as described above, anti-CEL I can be used for purification of CEL I and orthologs thereof (e.g., affinity column purification, immunoprecipitation).

CEL I protein may also be used to advantage in genetic screening assays as discussed above.

From the foregoing discussion, it can be seen that CEL I-encoding nucleic acids, CEL I expressing vectors, and anti-CEL I antibodies of the invention can be used to produce large quantities of CEL I protein, detect CEL I gene expression and alter CEL I protein accumulation for purposes of assessing the genetic and protein interactions involved in the recognition of DNA damage.

The following protocols are provided to facilitate the practice of the present invention.

Plasmid DNA pUC19 was isolated with the QIAGEN Maxi Kit from DH5 host cells, following the manufacturer's instructions. Calf thymus DNA was obtained from Sigma and purified by repeated cycles of proteinase K digestion and phenol extraction (9). Chromatography resins and columns were purchased from Pharmacia Biotech. Toluidine Blue O and Ponceau S were from Sigma. Endo $H_f$ was from New England Biolabs. Phosphocellulose P11 was from Whatman.

Purification of CEL I

All steps were performed at 4° C. The nuclease activity was monitored by using a RF-I (Replicative Form I) nicking assay (10).

Step 1: Preparation of the crude extract—105 kilograms of chilled celery stalks were homogenized with a juice extractor. The juice was collected (total 79.34 L) and adjusted to the composition of Buffer A (100 mM Tris-HCl, pH 7.7, 100 $\mu$M PMSF). Solid $(NH_4)_2SO_4$ was slowly and gently stirred into the juice, to a final concentration of 25% saturation. After 30 minutes, the suspension was centrifuged at 27,000×g for 1.5 hours. The supernatant (total 70.56 L) was pooled and the concentration of $(NH_4)_2SO4$ was adjusted to 80% saturation. After 30 minutes of stirring, the mixture was centrifuged at 27,000×g for 2 hours. The pellets were resuspended in Buffer B (0.1 M Tris-HCl, pH 7.7, 0.5 M KCl, 100 $\mu$M PMSF) and thoroughly dialyzed against Buffer B.

Step 2: Concanavalin A-Sepharose 4B affinity chromatography—100 ml of ConA resin (cross-linked with dimethylsuberimidate) was added to the 7.71 L sample in bottles that were gently rolled overnight. The resin was packed into a 2.5 cm diameter column. The flow-through fraction, containing no CEL I activity, was discarded. CEL I was eluted at 4 ° C. by 200 ml of Buffer B containing 0.3 M α-methyl-mannoside. The elution step was repeated 10 more times until no more nuclease activity could be eluted. The elutate was combined and dialyzed against Buffer C (50 mM Tris-HCl, pH 8.0, 5 mM α-methyl-mannoside, 0.01% Triton X-100, and 100 $\mu$M PMSF).

Step 3: DEAE-Sephacel chromatography—The dialyzed sample from step 2 (total 2.5 L) was applied to a 400 ml DEAE-Sephacel column of 5 cm diameter previously equilibrated with Buffer C. The subsequent steps were performed using FPLC. The column was washed with 400 ml of Buffer C. CEL I was eluted with a 1 L linear gradient of 10 mM to 1 M KCl in Buffer C containing 50 mM α-methyl-mannoside at a flow rate of 5 ml/min, followed by 400 ml of Buffer C containing 1 M KCl and 50 mM α-methylmannoside at a flow rate of 8 ml/min. The most active CEL I fractions were pooled and dialyzed against Buffer D (25 mM potassium phosphate, pH 7.0, 5 mM α-methyl-mannoside, 0.01% Triton X-100, and 100 μM PMSF).

Step 4: Phosphocellulose P-11 chromatography—The dialyzed CEL I pool from step 3 (120 ml) was applied to a 5 cm diameter column packed with 400 ml of P-11 resin. The column was previously equilibrated with Buffer D at a flow rate of 5 ml/min. After sample loading, the column was washed with 625 ml of Buffer D containing 50 mM α-methyl-mannoside at a flow rate of 5 ml/min. CEL I was eluted with a 800 ml linear gradient of 20 mM KCl to 1 M KCl in Buffer D containing 50 mM α-methyl-mannoside at a flow rate of 5 ml/min. The column was further washed with 400 ml of Buffer D containing 1 M KCl and 50 mM α-methyl-mannoside at a flow rate of 8 ml/min. The most active fractions were pooled and dialyzed against Buffer E (50 mM potassium phosphate, pH 7.0, 5 mM α-methyl-mannoside, 0.01% Triton X-100, and 100 μM PMSF) containing 1.5 M $(NH_4)_2SO_4$.

Step 5: Phenyl Sepharose CL-4B chromatography—The dialyzed CEL I pool from step 4 (480 ml) was applied to a 5 cm diameter column packed with 400 ml of Phenyl Sepharose CL-4B. The column was previously equilibrated with Buffer E containing 1.5 M $(NH_4)_2SO_4$ at a flow rate of 5 ml/min. After sample application, the column was washed with 400 ml of Buffer E containing 1.5 M $(NH_4)_2SO4$ and 50 mM α-methyl-mannoside at a flow rate of 5 ml/min. CEL I was eluted from the column with a 500 ml linear reversed salt gradient from 1.5 M to 0 M $(NH_4)_2SO_4$ in Buffer E containing 50 mM α-methyl-mannoside at a flow rate of 5 ml/min. The most active fractions were pooled and dialyzed against Buffer F (50 mM Tris-HCl, pH 8.0, 5 mM α-methyl-mannoside, 0.01% Triton X-100, and 100 mM PMSF).

Step 6: Mono Q anion-exchange chromatography—A Pharmacia prepacked Mono Q HR 16/10 column was thoroughly washed and equilibrated with Buffer F. The dialyzed CEL I pool from step 5 (336 ml) was applied at a flow rate of 5 ml/min followed by 100 ml of Buffer F containing 50 mM α-methyl-mannoside at a flow rate of 10 ml/min. CEL I was eluted with a 250 ml linear gradient of 0–1 M KCl in Buffer F containing 50 mM α-methyl-mannoside at 2 ml/min.

Step 7: Superdex 75 size-exclusion chromatography using the SMART system—The active fractions of step 6, fraction 11 and 12, were combined and concentrated by using Centricon 3 centrifugal concentrators. Aliquots of the concentrated enzyme were applied to a prepacked Superdex 75 PC 3.2/30 column equilibrated with Buffer G (50 mM Tris-HCl, pH 8.0, 100 mM KCl, 10 μM $ZnCl_2$, 0.01% Triton X-100, and 100 μM PMSF) containing 50 mM α-methyl-mannoside. Five ml of Buffer G containing 50 mM α-methyl-mannoside was used to elute CEL I at a flow rate of 0.05 ml/min. The purity of the active fractions was checked by SDS-PAGE. When additional protein bands were present, the fractions were pooled, concentrated, and purified again using the same size exclusion chromatography until CEL I reached apparent homogeneity.

SDS-Polyacrylamide Gel Electrophoresis (SDS-PAGE)

Polyacrylamide gel electrophoresis in SDS was carried out as previously described (11). Protein bands were detected by using the Gelcode Blue Stain Reagent (Pierce). Molecular weights of the protein bands were determined by using the semi-logarithmic plot of the molecular weights of protein standards versus their relative electrophoretic mobilities. Activity gel assay was performed essentially as described (12-13).

Endo $H_f$ Removal of N-linked Oligosaccharides from CEL I

CEL I sample was denatured in 0.5% SDS at 100° C. for 10 min. Appropriate amount of Endo $H_f$ was added and the reaction was incubated in GS buffer (50 mM Sodium Citrate, pH 5.5) at 37° C. overnight.

Renaturation of CEL I from SDS-PAGE

This method is a modification of a procedure previously described (13-14). The CEL I fractions were loaded onto the SDS-PAGE in two consecutive lanes. After electrophoresis, the gel was split between the two lanes. One half of the gel was stained with Gelcode Blue Stain Reagent (Pierce) and then aligned with the other half that was not stained. The gel slice corresponding to the CEL I band in the unstained gel was excised and eluted using an AMICON model 57005 electroeluter, for 2 hours at 20 mA per sample, using the elution buffer (50 mM Tris-HCl, pH 7.5, 180 mM NaCl, 0.1% SDS, 0.1 mg/ml BSA). After elution, the sample was concentrated by using a Centricon 3 unit. Centrifugation was overnight at 7,000×g. The volume of the sample was measured and 4 volumes of distilled acetone (−20° C.) was added. The sample was incubated in dry ice-ethanol bath for 30 min and then centrifuged at 14,000×g for 10 min. The precipitated proteins were washed with a buffer consisting of 20% Dilution and Renaturation Solution (50 mM Tris-HCl, pH 7.5, 10% Glycerol, 100 mM NaCl, 10 ml $MgCl_2$, 5 mM $CaCl_2$, 2 μM $ZnCl_2$ and 0.1 mg/ml BSA) and 80% acetone. The sample was precipitated again at 14,000×g for 10 min. The supernatant was discarded. The residual acetone was decanted by inverting the tube for 10 min. The pellet was air dried for at least 10 min. Twenty μl of Renaturation Solution (6 M Guanidine-HCl, 50 mM Tris-HCl pH 7.5, 10% Glycerol, 100 mM NaCl, 10 ml $MgCl_2$, 5 mM $CaCl_2$, 2 μM $ZnCl_2$ and 0.1 mg/ml BSA) was then used to dissolve the pellet. After 20 min of incubation at room temperature, 1 ml of Dilution and Renaturation Solution was added and the protein was further renatured at room temperature for 12 hours.

Mismatch Endonuclease Assay

The mismatch endonuclease assay was performed as previously described (8). Briefly, PCR products were amplified using genomic DNA from two individuals, one being wild-type and the other being heterozygous for C insertion in exon 20 in the BRCA1 gene. The forward primer was 5'-labeled with 6-FAM (blue) and the reverse primer was 5'-labeled with TET (green). The location of the insert in the BRCA1 gene is 5382 nt position. The resulting heteroduplexes provide 402 bp PCR products containing an extrahelical C or an extrahelical G. 50 ng of the fluorescently labeled substrate was incubated with CEL I for 30 min at 45 C. in a reaction volume of 20 μl in 20 mM HEPES pH 7.5, 10 mM KCl, 3 mM $MgCl_2$. The reactions were processed as described (8), loaded onto a denaturing 34 cm well-to-read 6% polyacrylamide gel on an ABI 377 DNA Sequencer and analyzed using GeneScan 3.1 software (Perkin-Elmer). The results are displayed as a gel image.

Preparation of the CEL I Sample for Sequencing

The purified CEL I sample was subjected to 10% SDS-PAGE analysis. After electrophoresis, the protein in the gel was electrophoretically transferred to an Immobilon-PSQ PVDF membrane by using a Western transfer apparatus (Novex). The transfer buffer contained 12 mM Trizma base, 96 mM glycine, and 20% methanol. The transfer condition was 1 hour at 25V (constant voltage). The membrane was next washed extensively with water, and stained with Ponceau S. The CEL I band was excised, destained with water, and sent to the Protein/DNA Technology Center of Rockefeller University for N-terminal and internal peptide microsequencing by automated Edman degradation reaction. The N-terminal sequence was determined first (15). The remaining protein fractions were digested with either Trypsin or GluC. The digested peptides were purified by HPLC, and sequenced with Edman Degradation (16).

Cloning of the cDNA of the CEL I mRNA

Total RNA was prepared from fresh celery using the phenol SDS method for, plant RNA preparation (17). First strand cDNA was synthesized using Stratagene's ProStar® First Strand RT-PCR kit. Degenerate PCR primers were chosen from the amino acid sequences determined by Edman degradation analysis of the pure CEL I protein, and used to amplify the CEL I cDNA in two segments, using the AMPLITAQ® DNA polymerase, and cloned in E. coli for DNA sequencing. The two fragments provided most of the reading frame of the CEL I protein. Using 5' and 3' RACE methods (Clonetech MARATHON™ cDNA amplification kit) the 5' and 3' coding regions and untranslated regions (UTR) OF CEL I cDNA were obtained. To confirm the authenticity of the cDNA, two PCR primers were designed, one in the 5' UTR, and one in the 3' UTR. These two primers were used to amplify the CEL I cDNA as one fragment from a fresh preparation of celery RNA, using the high fidelity Pfu DNA polymerase for the amplification. The new sequence was cloned in E. coli. The DNA sequence confirmed the authenticity of the previous cDNA sequence except for one nucleotide differenrce that gives another codon for the same amino acid.

Sources of Mung Bean Nuclease

Mung bean nuclease (MBN) was purchased from Pharmacia Biotech, #27-0912, herein called 'MBN-A', or purified as previously described (18), herein called 'MBN-B'. MBN assay conditions and the measurement of protein concentrations vary in different laboratories and may partially influence the quantitation in this study. MBN-A is FPLC purified, homogeneous, with a specific activity of $1.64 \times 10^6$ units/mg in the manufacturer's assay conditions, but $1.42 \times 10^6$ units/mg in our assay conditions. The enzyme exhibits a single-band in SDS PAGE. MBN-B is an older preparation of the original MBN of Kowalski and has a specific activity of $4 \times 10^5$ units/mg in the assay conditions described herein. The enzyme appeared as a single band of about 39 KDa on a non-reducing SDS PAGE (data not shown). One unit of MBN-A single-strand DNase activity equals 0.7 ng of enzyme in our assay.

RF-I Nicking Assay 1.1 $\mu$g of pPK201/cat (a pUC19 plasmid derivative, data not shown with pUC19 are similar) was incubated with the designated amount of MBN or CEL I for 30 minutes at 37° C. in a volume of 30 $\mu$l of Buffer H (20 mM sodium acetate pH 5.5, 10 mM KCl), or Buffer I (20 mM HEPES pH 7.5, 10 mM KCl) in the presence or absence of 3 mM $MgCl_2$. To stop the reaction, 5 $\mu$l of stop solution (50 mM Tris-HCl, pH 6.8, 3% SDS, 4.5% β-mercaptoethanol, 30% glycerol, and 0.001% Bromophenol Blue) was added. 24 $\mu$l of the final mixture was loaded onto a 0.8% agarose gel. After electrophoresis and staining with ethidium bromide, a photograph of the gel was taken and the negative was scanned using the IS-1000 Digital Imaging System (Alpha Innotech Corporation). The RF-I band was quantified using IS-1000 v2.02 software.

Single-strand DNase Assay

The DNA solubilization assay was similar to that previously described (19). Fifty $\mu$g of heat-denatured calf thymus DNA (Calbiochem #2618, purified by repeated pronase treatment, phenol extraction and dialysis) was incubated with 0.7 ng of MBN-A, or 1.9 ng of MBN-B, or 16 ng of CEL I, in 100 $\mu$l of Buffer H or Buffer I, with or without 3 mM $MgCl_2$. At the designated times, 100 $\mu$l of cold 20 mM $LaCl_3$ in 0.2 N HCl was added to stop the reaction. After centrifugation (21,000×g, 40 min), the absorbance at 260 nm of the supernatant was measured using a spectrophotometer to determine the amount of DNA that had become acid-soluble.

Mismatch Endonuclease Assay

The mismatch endonuclease assay was performed as previously described (8). Briefly, PCR products were amplified using genomic DNA of individuals that are heterozygous for certain alterations in three different exons in the BRCA1 gene. The forward primer was 5'-labeled with 6-FAM (blue) and the reverse primer was 5'-labeled with TET (green). The location of the mismatches in the BRCA1 gene are 300 nt, 4184 nt, 4421 nt, and 5382 nt positions. They correspond to a T→G base substitution in exon 5, a 4 base deletion in exon 11, a C→T polymorphism in exon 13, and a C insertion in exon 20, respectively. The four resulting heteroduplexes. provide a 235 bp PCR product containing a T/C or a G/A base-substitution mismatch, a 387 bp PCR product containing a 4 base loop, a 323 bp product containing either a C/A or a T/G base-substitution mismatch, and a 402 bp product containing an extrahelical C or an extrahelical G. 50 ng of the fluorescently labeled heteroduplex was incubated with 7 ng of MBN-A, or 11 ng of MBN-B, or 10 pg of CEL I (0.3 units) for 30 min at 37° C. or 45 C. in a reaction volume of 20 $\mu$l in Buffer I in the presence or absence of 3 mM $MgCl_2$. The reactions were processed as described (8), loaded onto a denaturing 34 cm well-to-read 6% polyacrylamide gel on an ABI 377 Sequencer and analyzed using GeneScan 3.1 software (Perkin-Elmer). The results are displayed as the peak profile of each lane of the gel image (FIG. 6).

Single-Strand RNase Assay

Fifty $\mu$g of purified Torula Yeast RNA (Amicon #7120) was incubated with 0.7 ng of MBN-A, or 16 ng of CEL I, in 100 $\mu$l of Buffer H or Buffer I, with 3 mM $MgCl_2$ at 37 C. At the designated times, 13 $\mu$l of cold 3M sodium acetate pH 5.2 and 282 $\mu$l of ethanol was added. The mixture was put at −20° C. overnight. After centrifugation to precipitate the RNA (21,000×g, 45 min), the absorbance at 260 nm of the supernatant was measured using a spectrophotometer to determine the amount of RNA that had become soluble.

The following examples are provided to describe the invention in further detail. These examples, which set forth the best mode presently contemplated for carrying out the invention, are intended to illustrate and not to limit the invention.

EXAMPLE I

Purification of CEL I

Figure 8:
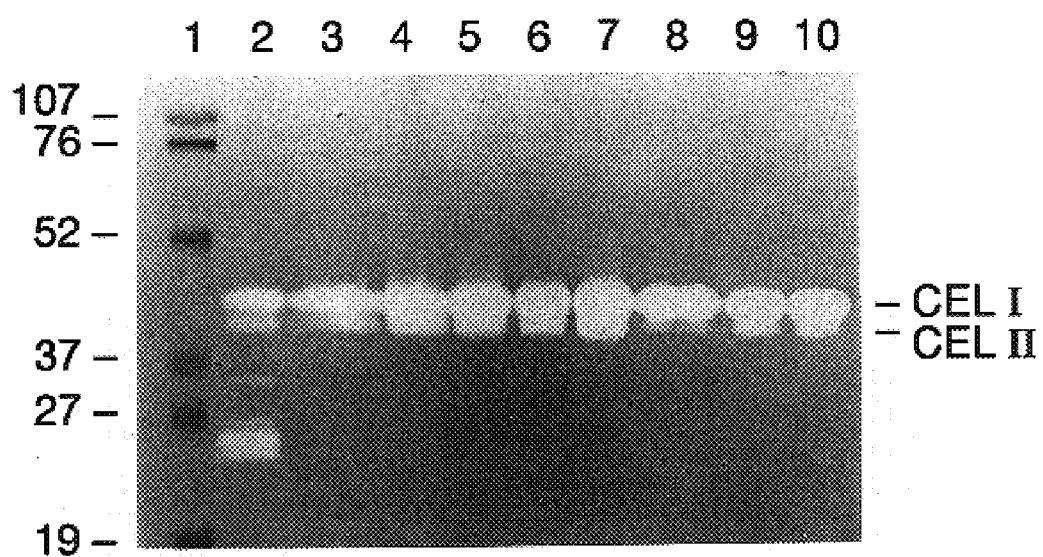
FIG. 8 is a gel showing polyacrylamide gel analysis of the CEL I purification fractions. Aliquots of CEL I with approximately equal amounts of CEL I activity from each step of enzyme purification was boiled in SDS gel buffer in the absence of reducing agents, and resolved on a SDS polyacrylamide gel as detailed in the experimental procedures. The nucleases, after renaturation, digested the denatured DNA embedded in the gel. The undigested DNA was stained with Toluidine Blue O to provide a negative image of the positions of the nucleases. Lane 1: molecular weight markers; Lane 2: buffered celery juice; Lane 3: 25% ammonium sulfate fractionation supernatant; Lane 4: 80% ammonium sulfate fractionation pellet; Lane 5: sample to ConA Sepharose column; Lane 6: eluate from ConA Sepharose column; Lane 7: eluate from DEAE-Sephacel column; Lane 8: eluate from Phosphocellulose P-11 column; Lane 9, eluate from Phenol Sepharose column; Lane 10: pool of fractions 11 and 12 from Mono Q column.

CEL I was purified to homogeneity, more than 33,000 fold over its specific activity in the buffered celery juice. Table 1 summarizes the purification of CEL I from 105 Kg of celery stalks. The active band of CEL I is of the same size throughout purification as judged by an activity gel assay. See FIG. 8. There are two nuclease bands that copurify during all the purification steps. We show below that the minor band is not derived from the major band. The major nuclease activity, designated CEL I, migrates at 43 KDa on SDS PAGE (FIG. 1A). The minor activity at 39 KDa is a putative isozyme we named CEL II FIG. 1C, lane 3), also capable of cutting at mismatches.

TABLE I

| Purification Step | Volume in Liter | Total Protein, mg | Total Activity, CEL I units | Specific Activity, units/mg | Protein, Fold-Purification |
|---|---|---|---|---|---|
| Buffered Juice | 79.34 | 19,399 | $1.9 \times 10^7$ | $9.7 \times 10^2$ | |
| 25% $(NH_4)_2SO_4$ Supernatent | 70.56 | 17,005 | $1.6 \times 10^7$ | $9.2 \times 10^2$ | 1 |
| 80% $(NH_4)_2SO_4$ pellet | 8 | 2,072 | $9.0 \times 10^6$ | $4.4 \times 10^3$ | 4.5 |
| ConA-Sepharose 4B | 2.5 | 6.75 | $3.6 \times 10^6$ | $5.4 \times 10^5$ | 553.8 |
| DEAE-Sephacel | 0.12 | 2.69 | $2.4 \times 10^6$ | $8.8 \times 10^5$ | 907.6 |
| Phospho-cellulose P-11 | 0.48 | 0.408 | $1.5 \times 10^6$ | $3.8 \times 10^6$ | 3,854 |
| Phenol Sepharose CL-4B | 0.34 | 0.054 | $5.6 \times 10^5$ | $1.0 \times 10^7$ | 10,676 |
| Mono Q | 0.03 | 0.03 | $3.6 \times 10^5$ | $1.2 \times 10^7$ | 12,316 |
| Superdex 75 | 0.0005 | 0.005 | $3.1 \times 10^5$ | $3.1 \times 10^7$ | 33,000 |

EXAMPLE 2

Isoelectric Point of CEL I and CEL II

A sample of CEL I, containing a small amount of CEL II, was loaded onto an isoelectric focusing gel (pH 3–10, from Novex). After the gel was stained, the pI of the CEL I and CEL II were obtained by comparison with the standards (Bio-Rad). The pI of the CEL I band was between 6.0 and 6.5, and the pI of the CEL II band was between 6.5 and 6.8 (data not shown). After minimizing the N-linked oligosaccharides by Endo $H_f$, the 43 KDa major celery nuclease band shifted to the 29 KDa position (FIG. 1B & C, lanes 4) and the 39 KDa minor celery nuclease band shifted to the 37 KDa position (FIG. 1C, lane 4). If CEL II were a degradation product of CEL I, after endo $H_f$ treatment, its polypeptide length should be equal or less than 29 KDa.

EXAMPLE 3

Effects of Reducing Agents on CEL I

When 1% -mercaptoethanol was used in the sample buffer for SDS-PAGE analysis of the CEL I band, CEL I was shifted upward (FIG. 1D, lane 2) but intact. DTT was also tested and similar results were obtained (data not shown). The simplest interpretation is that the CEL I polypeptide does not contain any breakage in the backbone. Instead, disulfide bonds were broken that resulted in the enzyme becoming more extended in the reduced state, and hence slower in electrophoretic mobility.

EXAMPLE 4

Renaturation of Homogeneous CEL I and CEL II

Figures 9A, 9B:
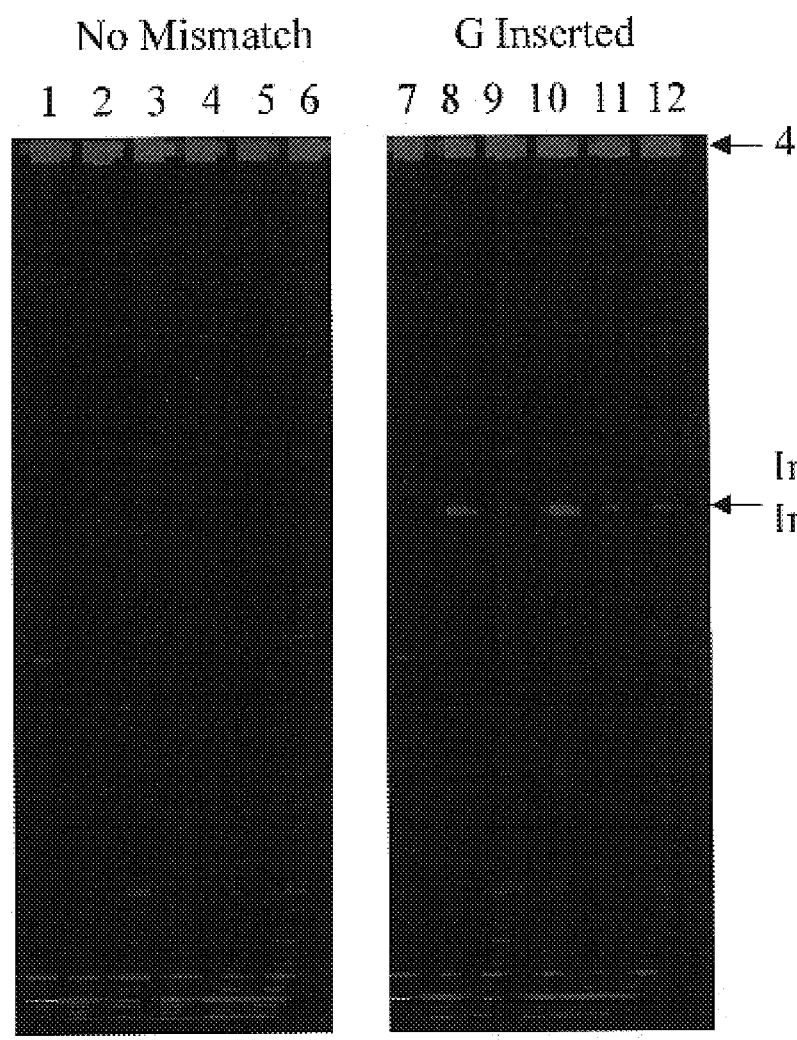
FIGS. 9A and 9B are a pair of gels showing incision at mismatch substrate by CEL I, CEL II proteins renatured from SDS gel, before and after removal of carbohydrate moieties. CEL I and CEL II protein bands were excised from a SDS gel and renatured as described in experimental procedures. The renatured enzyme was used to digest a 402 bp fluorescently labeled PCR product of exon 20 of the BRCA 1 gene. Lanes 1–6 are homoduplexes made from wild-type DNA samples containing no mismatch in exon 20. Lanes 7–12, because of the heterozygous nature of this sequence in the sample, the PCR product is a heteroduplex in which one strand contains a G residue insertion. Cel I incision at the 3' side of the extrahelical G residue produces a green band, indicated in the figure as "incision at inserted G." Lanes 1 and 7: substrate with no CEL I treatment; Lanes 2 and 8: incision of the substrate by purified native CEL I; Lanes 3 and 9: incision of substrate by renatured 29 KDa CEL I polypeptide band originated from $EndoH_f$ digestion of the 43 KDa CEL I band; Lanes 4 and 10: incision of the substrate by the renatured 37 KDa CEL II polypeptide band originated from $EndoH_f$ digestion of the 39 KDa CEL II band; Lanes 5, 6, 11, and 12: incision of the substrate by renatured 43 KDa CEL I band.

Individual celery nuclease bands were excised from the 10% SDS-PAGE and eluted as described in above. These bands included the 43 KDa band, the 39 KDa band, and their corresponding bands after the Endo $H_f$ digestion. The eluted enzyme fractions were concentrated and renatured. Plasmid nicking assays were carried out to show that the renatured samples were all active nucleases. See FIG. 9. The renatured CEL I before or after Endo $H_f$ digestion and CEL II after Endo $H_f$ digestion were able to incise DNA at a mismatch substrate. In this experiment, the mismatch incised is a G residue insertion. This experiment is necessarily qualitative because of the uncertainties in the recovery of proteins and activity in the gel elution and renaturation steps. However, the data strengthens the conclusion that CEL I and CEL II are homogeneous and each able to incise at a DNA mismatch, and that most of the carbohydrates on CEL I and CEL II are not essential for activity.

EXAMPLE 5

The Cloning of CEL I cDNA

The amino acid sequence of the N-terminal and three other internal proteolytic peptides of CEL I, identified by Edman degradation performed by the Protein/DNA Technology Center of the Rockefeller University, are shown in FIG. 2 in bold letters. The 72 amino acids identified represent about 28% of the CEL I polypeptide and were completely accounted for in the cDNA sequence. CEL I without the leader sequence is a protein of 274 amino acid residues, with a calculated molecular weight of 31,440.2. Compared with the apparent molecular weight of 43 KDa determined in SDS PAGE, CEL I is 27 percent carbohydrate by weight.

Alignment of CEL I cDNA amino acid sequence (SEQ ID NO: 2, residues 23–296) with homologs in Genbank by the PSI-Blast program at NCBI (20) revealed that CEL I has relative low identity to the Aspergillus S1 nuclease (accession P24021, SEQ ID NO: 7, 27% of 273 amino acids) and P1 nuclease (accession P24289, SEQ ID NO: 8, 30% of 277 amino acids), see FIG. 10. However, among all the homologs of CEL I in plants, three stand out to be of very high degree of identity. Namely, ZEN1 (accession AB003131, SEQ ID NO: 9, 80% identity of 269 amino acids), DSA6 (accession AF082031, SEQ ID NO: 10, 73% of 271 amino acids), BFN1 (accession U90264, SEQ ID NO: 11, 72% identity of 274 amino acids). We propose that these three proteins are probably orthologs of CEL I because all other homologs are at a range of 45% identity or lower. Moreover, when one superimposes the sequence of CEL I and these three orthologs on the secondary structure of P1 nuclease, most of the sequence differences among these four putative orthologs are in the flexible loop regions that connect consecutive helices (FIG. 10) and in the flexible COOH terminal-region. Thus it is very likely that these orthologs share the enzymatic properties of CEL I and substrate specificity of the S1 nuclease.

EXAMPLE 6

Mg++ and pH Dependence of CEL I

A gel-image of the automated DNA sequencer analysis of the CEL I incision at the mismatch of a T→G base substitution is shown in FIG. 3. Lanes 1–4 are mock reactions without CEL I. The full length 235 nt PCR product is seen on top of the image, and imperfect PCR products are seen as the bands dispersed below. In lane 5, in the presence of CEL I, MG++ and pH 7.5, the blue incision band of 156 nt and the green incision band of 80 nt are observed as indicated. In the absence of Mg++ or in pH 5.5 (Lanes 6–8), mismatch-specific incisions are not significant. This experiment also illustrates how the imperfect PCR byproducts seen in lanes 1–4 are eliminated by CEL I in lanes 5–8, especially under the conditions of lane 5.

EXAMPLE 7

The RF-I Nicking Activity of CEL I and MBN

Supercoiled plasmid replicative form I (RF-I) DNA exhibit local regions of instability in the double-helix that can be attacked by nucleases. Upon the first nick, the superhelical stress is relieved, and the DNA is no longer a substrate for most single-strand nucleases. The RF-I nicking activities of MBN and CEL I at pH 5.5 versus pH 7.5 are shown in FIG. 4. Panel A and B compare the nicking of RF-I by MBN-A at the two pH's in the presence and absence of $Mg^{++}$. In panel A, under condition of initial kinetics, the inhibition of MBN by 3 mM $Mg^{++}$ is about 90%. About 70% of the RF-I is nicked by 7 pg of MBN-A in 30 min at pH 5.5. In panel B, 7 ng of MBN-A can only nick about 20% of the RF-I in 30 min at pH 7.5. Similar result is obtained for MBN-B in panels C and D. Similar comparison of CEL I RF-I nicking activity is shown in panel E for pH 5.5, and panel F for pH 7.5. The data shows that CEL I is about twice as active in RF-I nicking in the presence of $Mg^{++}$ than in the absence of $Mg^{++}$. Comparing the 5 pg data points, CEL I is twice more active at pH 7.5 than at pH 5.5.

EXAMPLE 8

The single-strand DNase Activity of CEL I and MBN

Figure 5A:
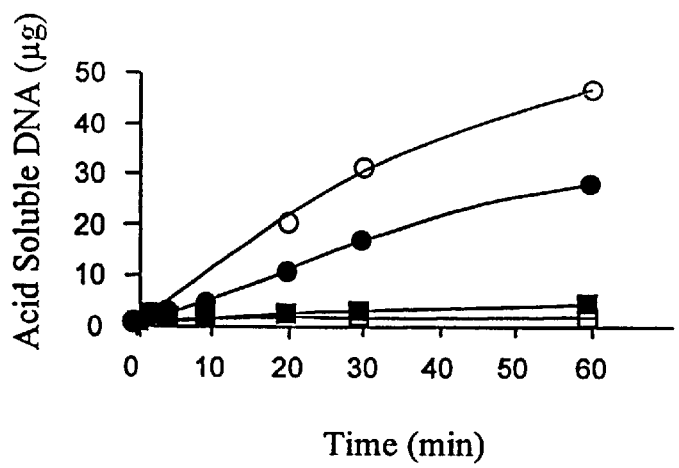
FIGS. 5A–5C show the solubilization of denatured calf-thymus DNA by CEL I and mung bean nuclease. Assays are in the presence (solid symbols) or absence (hollow symbols) of 3 mM $MgCl_2$. Circles are assays at pH 5.5. Squares are at pH 7.5. The enzymes tested in panels A, B, and C are MBN-A, MBN-B, and CEL I, respectively. One unit of single-strand nuclease activity of CEL I equals 32 ng of homogeneous CEL I ($3.1 \times 10^4$ single-strand nuclease units/mg enzyme as seen in initial kinetics up to 20 min in panel C).
Figure 5B:
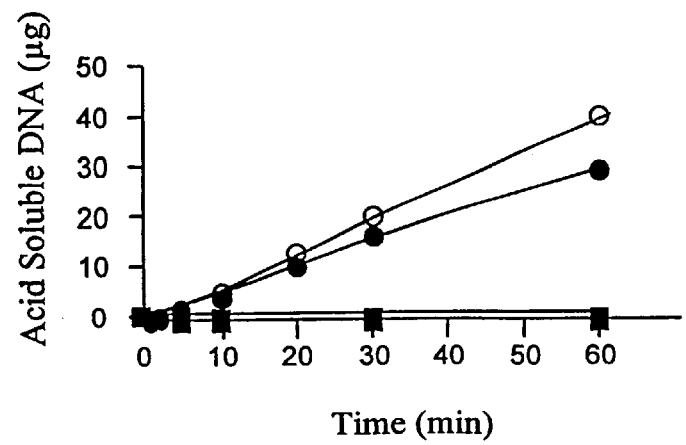
Figure 5C:
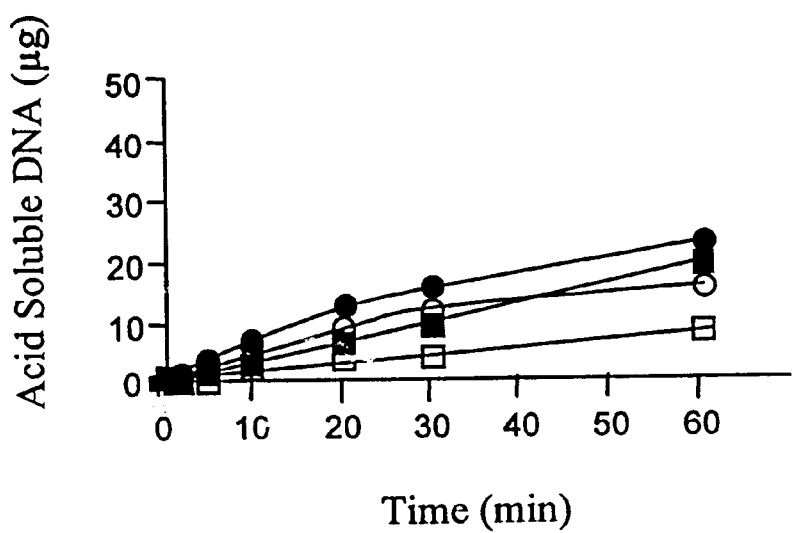

The digestion of denatured purified calf thymus DNA by MBN and CEL I is shown in FIG. 5. For ease of comparison, different amounts of MBN and CEL I were used so that the assays are in a similar range of total activity. The amounts of enzyme used for MBN-A, MBN-B, and CEL I were 0.7 ng, 1.9 ng, and 16 ng, respectively. The lack of activity by MBN at pH 7.5 is obvious in panels A and B. The $Mg^{++}$ inhibition of MBN is also observed for the activity on single-stranded DNA. In contrast, CEL I is more active in the presence of $Mg^{++}$ than in the absence. Importantly, comparing the initial kinetics in panels A and C for the highest activity condition for each enzyme, MBN-A in the absence of $Mg^{++}$ at pH 5.5 appears to be about 32 times higher in single-strand nuclease specific activity than for CEL I in the presence of $Mg^{++}$ at pH 5.5 ($1.42 \times 10^6$ g DNA solubilized/min/mg protein versus $4.46 \times 10^4$ g DNA solubilized/min/mg protein).

EXAMPLE 9

The Mismatch Endonuclease Activity of CEL I and MBN

The nicking of DNA duplexes containing mismatches by MBN and CEL I is shown in FIG. 6. The mismatch with a four base loop is nicked by CEL I and both preparations of MBN at pH 7.5 (A, B, C). Note the higher amounts of MBN needed in this reaction. However, even at 1000 times more enzyme than CEL I, MBN is unable to specifically nick at base-substitutions at a single base mismatch (D, E, G, and H). When the same amount of MBN protein is incubated with DNA substrates at pH 5.5 as at pH 7.5 the substrate is almost completely digested (data not shown). When a lesser, more appropriate amount of MBN is incubated with the DNA substrate at pH 5.5, no mismatch-specific nicking is seen (data not shown). CEL I nicks at the base-substitution mismatch (panel F) and at the extrahelical nucleotide (panel I). In panel F, the blue peak at position 183 nt corresponds to the nick at the 3' side of the mismatch on the 6-FAM-labeled strand of the heteroduplex, and the green peak at position 142 nt corresponds to the nick at the 3' side of the mismatch on the TET-labeled strand. Some of the other blue peaks are non-specific cutting by CEL I; it is important to note that if one incubates the reaction for a longer time, or with more CEL I enzyme, most of these non-mismatch specific peaks will be removed while the mismatch-specific peaks will remain (FIG. 3). The reason is that these background bands are often non-specific heteroduplexes of PCR products in which the two DNA strands do not basepair properly. These duplexes are nicked by CEL I at non-specific positions, and their signal becomes diffused. In panel I, the green peak at 252 nt corresponds to the nick at the 3' side of the extrahelical G on the TET-labeled strand of the PCR product. A blue peak corresponding to the nick at the extrahelical C on the 6-FAM-labeled strand is expected at position 151 nt, but is not seen. CEL I may have nicked the 6-FAM-labeled strand near its 5'-end removing the dye, making it unable to score the blue peak in the assay. Alternatively, the insert C substrate may have been outcompeted by the insert G substrate.

EXAMPLE 10

The RNase Activity of CEL I and MBN

Figure 7A:
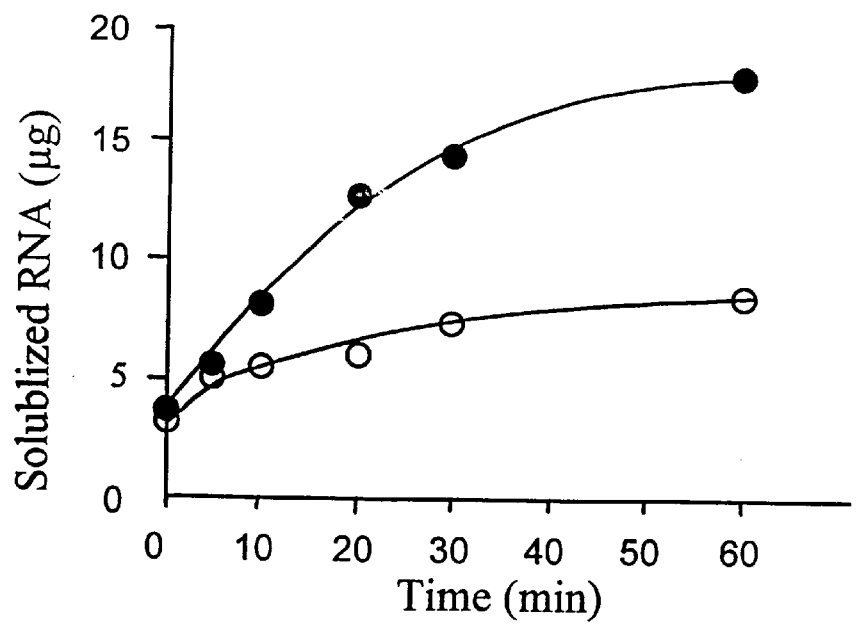
FIG. 7 shows the solubilization of RNA by CEL I and mung bean nuclease. Torula yeast RNA was incubated with 0.7 ng of MBN-1 (solid circles) or 16 ng of CEL I (hollow circles) in the presence of 3 mM $MgCl_2$ at pH 5.5 (A) and pH 7.5 (B).
Figure 7B:
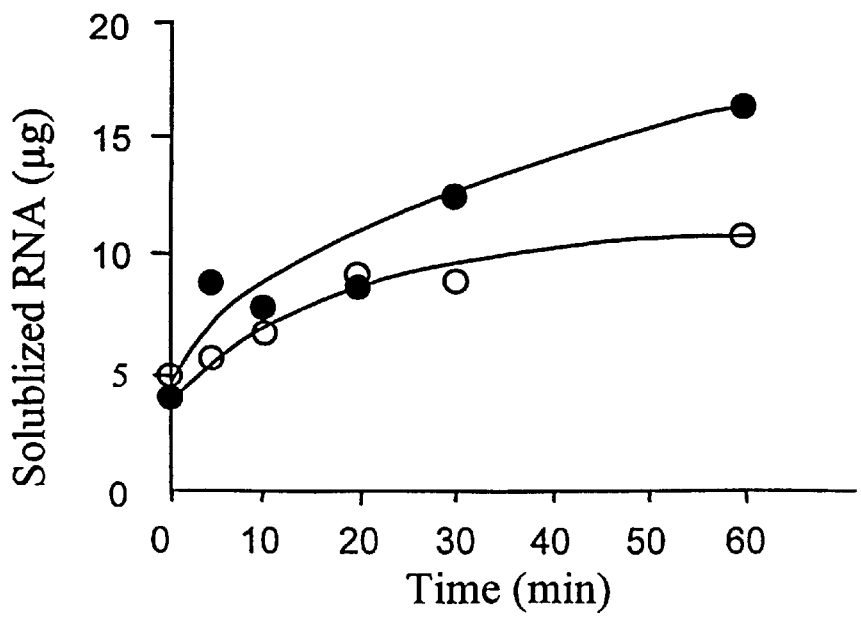

A property common to S1 and CEL I is the ability to digest both RNA and DNA, a feature referred to as "sugar non-specific" or "bifunctional" in literature. We have compared the specific activities of MBN and CEL I on RNA using conditions comparable to their DNase activities. The specific questions addressed here are whether the RNase activity is pH-dependent, and whether the specific activities of the RNase and DNase are similar for each enzyme. Our assay measures the digestion of RNA to soluble nucleotides and short RNA fragments. The specific activity of the RNase activity of MBN-A (FIG. 7A) is comparable to its single-strand DNase activity (FIG. 5A). The specific activity of CEL I is 50 times less than MBN-A on Torula Yeast RNA (FIG. 7A) at pH 5.5. This value is consistent with our finding that CEL I is about 32 times lower in specific activity than MBN-A using denatured calf-thymus DNA as substrate. CEL I as an RNase is slightly more active at pH 7.5 than at pH 5.5. This is opposite to the observation for the single-strand DNase activity of CEL I, but the differences are small. Thus MBN at pH 5.5, and CEL I at pH 5.5 and pH 7.5, showed no preference for RNA versus DNA. MBN-A digested RNA at pH 7.5 with the same specific activity as at pH 5.5 (FIG. 7). This is in striking contrast to MBN-A's little to no ability to digest single-stranded DNA at pH 7.5 (FIG. 5A). Similar results were found for the RNase activity of MBN-B (data not shown).

Discussion

The Purification of Glycoproteins

We previously described a purification protocol that produced highly enriched CEL I, however the enzyme never appeared as a single band on a SDS PAGE gel (8). To identify the source of contamination, we repeated the purification with *Arabidopsis callus,* and observed the same problem of aggregation. We made mouse antibodies to the purest fraction and used the antiserum to identified clones of two different genes from an Arabidopsis cDNA expression library (21) (accession # AC001645, genes PID:g2062157 and PID:g2062159) (unpublished data). These clones were found to be highly homologous to two jasmonate inducible proteins of *Brassica napus* that are known to function as ConA-like lectins accession # CAA72271, 62% identity in 475 amino acids) (22). Such lectins are coded for by over 30 genes in Arabidopsis and can be a problem when the glycoprotein to be purified is less abundant than the lectins. The presence of mannose in the buffers in the present protocol has overcome this obstacle and has provided a homogeneous preparation of CEL I.

Alignment of CEL I Amino Acid Sequence

In an alignment of CEL I amino acid sequence with all the S1 homologs in Genbank, (FIG. 10), the universally conserved residues are the N-terminal tryptophan residue, five histidine residues, and three aspartate residues, located in different regions of the polypeptide (FIG. 2). These nine residues are brought together to bind the three $Zn^{++}$ atoms, as revealed by the X-ray crystallography structure of the P1 nuclease (23–24). The conservation of the catalytic active site suggests that these nucleases share the same mechanism for the cleavage of the phosphodiester bonds, necessitating the conservation of the enzyme structure to form the catalytic domain. The differences in substrate preference may lie in the mechanism of substrate recognition, separate from catalysis, such that S1 family nucleases are specific for single-stranded nucleic acids whereas CEL I shows high specificity for mismatch heteroduplexes. The sequences that enable the recognition of different substrates may reside in amino acid sequences that are less conserved. To better define the catalytic differences of CEL I and S1 type nucleases, we performed a careful contrast of CEL I with MBN, the best characterized ortholog of S1 nuclease in plant.

The pH Dependence of CEL I and Mung Bean Nuclease

In the RF-I of plasmid pUC19, supercoiling induces regions of single-strandedness that can become a substrate for nucleases. Moreover, regions such as the origin of replication are known to form stem-loop structures. It has also been shown that there are destabilized sequences in supercoiled plasmids (25). The data in FIG. 4 demonstrated that MBN nicks RF-I more quickly at pH 5.5 than at pH 7.5 by more than 1000 fold, yet CEL I is more active at pH 7.5 than at pH 5.5.

The >1000 fold higher activity of MBN at acidic pH on RF-I cutting may be a function of the catalytic mechanism of the enzyme. Another factor that contributes to faster rate of RF-I nicking at acidic pH may be the partial unwinding of a plasmid at acidic pH, thereby producing a greater propensity for single-strandedness. In the case of CEL I being active on plasmid RF-I at neutral pH, one may speculate that a partial unwinding of the RF-I occurs upon the binding of CEL I. Alternatively, CEL I may not be recognizing single-strandedness in the plasmid. The reason is that in spite of CEL I being more active in the digestion of single-stranded DNA at pH 5.5 than at pH 7.5 (FIG. 5), CEL I is less active in RF-I nicking at pH 5.5 than at pH 7.5 (FIG. 4).

Figure 6A:
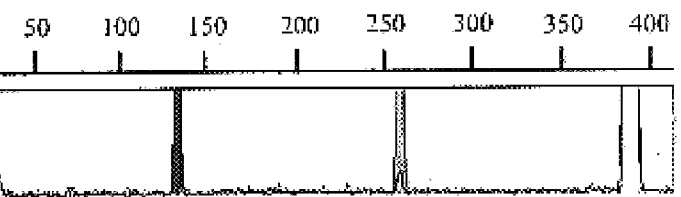
FIGS. 6A–6I are electropherograms comparing mismatch detection mediated by CEL I and MBN. Electropherograms of Genescan fragment analysis on an PE-Biosystems automated DNA sequencer are shown. Two color fluorescent heteroduplexes of PCR products of BRCA1 gene were prepared as described in the experimental procedures. Vertical axis, relative fluorescence units; horizontal axis, DNA length in nucleotides. In Panels A, D, and G, the DNA was incubated with 7 ng of MBN-A. In Panels B, E, and H, the DNA was incubated with 11 ng of MBN-B. In Panels C, F, and I, the DNA was incubated with 10 pg of CEL I. These reactions were performed in Buffer I with 3 mM $MgCl_2$ for 30 min at 37 C. In panels A, B, and C, the substrate was a 387 bp heteroduplex containing a 4 nt deletion. In panels D, E, and F, the substrate was a 323 bp product containing a C→T base substitution mismatch. In panels G, H, and I, the substrate was a 402 bp heteroduplex containing a C insertion in one strand. In each of panels A, B, and C the peak at 129 nt corresponds to cutting at the 4 base insertion on the 6-FAM-labeled strand; the peak at 258 nt corresponds to the cutting at the 4 base insertion on the TET-labeled strand. In -panels D, E, G, and H, no mismatch-specific cutting is seen by the two MBN3 s. In panel F, the peak at 183 nt corresponds to CEL I-mismatch-specific cutting on the 6-FAM-labeled strand, and the peak at 142 nt corresponds to the mismatch-specific cutting on the TET-labeled strand. In panel I, the peak at 252 nt corresponds to the CEL I specific cutting at the extrahelical G on the TET-labeled strand.
Figure 6B:
Figure 6C:
Figure 6D:
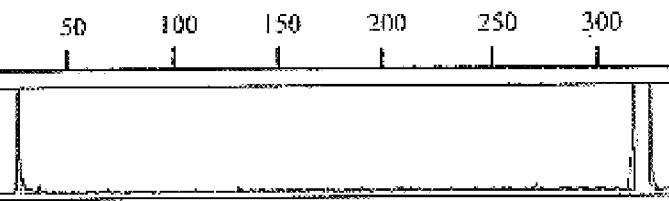
Figure 6E:
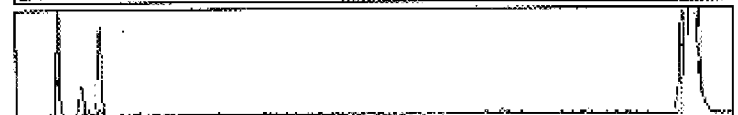
Figure 6F:
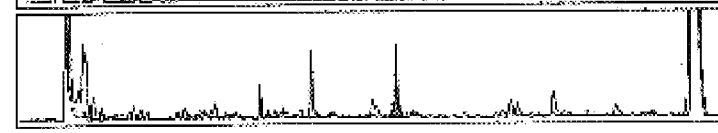
Figure 6G:
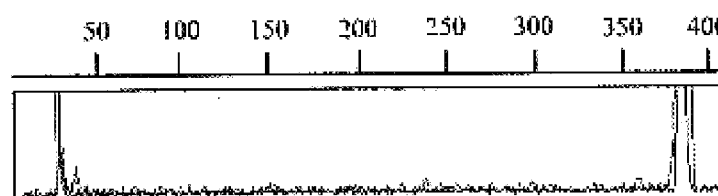
Figure 6H:
Figure 6I:

When CEL I uses denatured DNA as a substrate, the specific activity of CEL I is 20 times less than MBN-A (FIG. 5C) at acidic pH and only slightly improved at pH 7.5 in the presence of $Mg^{++}$. In RF-I nicking, which reflects the recognition of destabilized helices, CEL I specific activity is only 2 times less than MBN-A at pH 5.5, but CEL I is 1000 times more active at pH 7.5 (FIG. 4). Moreover, CEL I nicks a mismatch heteroduplex containing four extrahelical bases at 700 times higher specific activity than MBN-A (FIG. 6A, B, C). Lastly, only CEL I can nick DNA at base-substitutions. Therefore, it is evident that CEL I is not primarily a single-strand DNase. Moreover, single-strandedness per se is not what CEL I recognizes in a mismatch substrate.

The Role of $Mg^{++}$ in the Activity CEL I and the MBN

The initial rate of RF-I nicking by MBN at pH 5.5 is inhibited by $Mg^{++}$ by about 10 to 20 fold. In contrast, CEL I is stimulated by $Mg^{++}$ under all assay conditions. The CEL I nicking of RF-I significantly increases in the presence of $Mg^{++}$ at both pH's. By the RF-I nicking assay itself, it is not possible to distinguish whether the effect of the $Mg^{++}$ is on the plasmid DNA structure or on the enzyme. With single-stranded DNA as substrate, the effect of $Mg^{++}$ on the enzymes was lower perhaps because the effects of $Mg^{++}$ on substrate superhelicity is not involved. With the mutation detection assay, it is clear that $Mg^{++}$ is required for optimal CEL I incision at mismatches in double-stranded DNA (FIG. 3). If CEL I and MBN should use the same catalytic mechanism for phosphodiester bond cleavage, their differences may lie in how the substrates are recognized. The role of $Mg^{++}$ may lie in a structural role for substrate recognition and not in DNA hydrolysis (26). Lastly, both MBN and CEL I are observed to be RNases. Surprisingly, MBN is primarily an RNase at neutral pH with the RNase activity at least one thousand times greater than the DNase activity.

Thus it is clear that MBN and CEL I represent two different enzyme families within the S1 superfamily of structurally related nucleases. The high resolution X-ray structure of the P1 nuclease showed that a double stranded helix cannot fit into the P1 DNA binding grove (21-22).

In summary, it appears that CEL I exemplifies a unique family of mismatch recognizing nucleases. Additionally, based on marked sequence similarity, it appears that CEL I ortholog sequences may be also used to advantage in the assay methods for mutation detection as described herein for CEL I.

References

1. Nucleases, eds. Linn, S. M., Lloyd, R. S., and Roberts, R. J. Cold Spring Harbor Laboratory Press, 1993.
2. Kowalski, D., Kroeker, W. D., and Laskowski, M. Sr. (1976) *Biochemistry* 15, 4457–4462
3. Sung, S., and Laskowski, M., Sr. (1962) *J. Biol. Chem.* 237, 506–511
4. Kowalski, D., Natale, D. A. and Eddy, M. J. (1988) *Proc. Natl. Acad. Sci. USA* 85, 9464–9468
5. Shank, T. E., Rhodes, C. Rigby, P. W. J., and Berg, P. (1975) *Proc. Nat. Acad. Sci. USA,* 72, 989–993
6. Maekawa, K., Tsunasawa, S., Dibo, G., and Sakiyama, F. (1991) *Eur. J. Biochem.* 200, 651–661
7. Lacks, S. A. (1981) *J. Biol. Chem.* 256, 2644–2648
8. Oleykowski, C. A., Bronson Mullins, C. R., Godwin, A. K., and Yeung, A. T. (1998) *Nucleic Acids Research,* 26, 4597–4602
9. Sambrook, J., Fritsch, E. F., and Maniatis, T. (1989) Molecular Cloning: A Laboratory Manual, 2nd Ed., Cold Spring Harbor Laboratory, Cold Spring Harbor, N.Y.
10. Yeung, A. T., Mattes, W. B., Oh, E. Y., and Grossman, L. (1983) *Proc. Natl. Acad. Sci. USA* 80, 6157–6161
11. Laemmli, U. K. (1970) *Nature* 227, 680–685
12. Blank, A., Silber, J. R., Thelen, M. P., and Dekker, C. A. (1983) *Anal. Biochem.* 135, 423–430
13. Hager, D. A., and Burgess, R. R. (1980) *Anal. Biochem.* 109, 76–86
14. Kennedy, J. F., Robertson, E. R. (1996) *Bioseparation* 6, 1–15
15. Fernandez, J., Gharahdaghi, F., and Mische, S. M. (1998) *Electrophoresis.* 19, 1036–1045
16. Fernandez, J., Andrews, L., and Mische, S. M. (1994) *Anal Biochem.* 218, 112–117
17. Current Protocols in Molecular biology, Ausubel, F. M., Brent, R., Kingston, R. E., Moore, D. D., Seidiman, J. G., Smith, J. A., and Struhl, K. eds. John wiley & Sons, N.Y. 1989.
18. Kowalski, D., Kroeker, W. D., and Laskowski, M. Sr. (1976) *Biochemistry* 15, 4457–4462
19. Sung, S., and Laskowski, M., Sr. (1962) *J. Biol. Chem.* 237, 506–511

20. Altschul, S. F., Madden, T. L., Schaffer, A. A., Zhang, J., Zhang, Z., Miller, W. & Lipman, D. J. (1997) *Nucleic Acids Res.* 25, 3389–3402.
21. Kieber, J. J., Rothenberg, M., Roman, G., Feldmann, K. A., Ecker, J. R. (1993) *Cell* 72, 427–441
22. Geshi, N., Brandt, A. (1998) *Planta* 204, 295–304
23. Volbeda, A., Lahm, A., Sakiyama, F. and Suck, D. (1991) *EMBO J.* 10, 1607–1618
24. Romier, C., Dominguez, R., Lahm, A., Dahl, O., and Suck, D. (1998) *Proteins: structure, Function, and Genetics* 32, 414–424
25. Kowalski, D., Natale, D. A. and Eddy, M. J. (1988) *Proc. Natl. Acad. Sci. USA* 85, 9464–9468
26. Katz, A. K., and Glusker, J. P. (1998) *Adv. in Mol. Structure Res.* 4, 227–279
27. Oleykowski, C. A., Bronson Mullins, C. R., Chang, D. W., and Yeung, A. T. (1999) *Biochemistry* 38, 2200–2205.
28. Panavas, T., Pikula, A., Reid, P. D., Rubinstein, B., and Walker, E. L. (1999) *Plant Molecular Biology* 40, 237–248.

While certain preferred embodiments of the present invention have been described and specifically exemplified above, it is not intended that the invention be limited to such embodiments. Various modifications may be made to the invention without departing from the scope and spirit thereof as set forth in the following claims.

What is claimed is:

1. An isolated nucleic acid molecule having the sequence of SEQ ID NO: 1, said nucleic acid molecule encoding an endonuclease protein from celery about 309 amino acids in length, said encoded protein comprising a plurality of α helix domains and a flexible carboxy terminal region.

2. The nucleic acid molecule of claim 1, which is DNA.

3. The DNA molecule of claim 2, which is a cDNA comprising a sequence approximately 1135 base pairs in length that encodes said endonuclease protein.

4. An isolated RNA molecule transcribed from the nucleic acid of claim 1.

5. An isolate polynucleotide which comprises:
   a) a sequence encoding a protein as defined in claim 1;
   b) a sequence encoding the complete complementary and;
   c) a sequence encoding SEQ ID NO:2.

6. An oligonucleotide consisting of between about 25 and about 200 contiguous nucleotides of SEQ ID NO: 1 or the complete complement thereof, which specifically hybridizes under high stringency conditions in 6×SSC, 5×Denhardt's solution, 0.5% SDS and 100 μg/ml denatured salmon sperm DNA at 42° C., and wash in 1×SSC and 0.5% SDS at 65° C. for 15 minutes with SEQ ID NO: 1 or the complete complement thereof.

7. An isolated nucleic acid molecule encoding an endonuclease having the sequence of SEQ ID NO: 2.

8. A plasmid comprising an isolated nucleic acid sequence having the sequence of SEQ ID NO: 1.

9. A vector comprising an isolated nucleic acid sequence having the sequence of SEQ ID NO: 1.

10. A retroviral vector comprising an isolated nucleic acid sequence having the sequence of SEQ ID NO: 1.

11. An isolated host cell comprising an isolated nucleic acid molecule having the sequence of SEQ ID NO: 1.

12. An isolated host cell as claimed in claim 11, wherein said host cell is selected from the group consisting of bacterial, fungal, mammalian, insect and plant cells.

* * * * *